United States Patent
Sokal et al.

(10) Patent No.: US 7,824,383 B2
(45) Date of Patent: Nov. 2, 2010

(54) VAGINAL DRUG DELIVERY SYSTEM AND METHOD

(75) Inventors: David C. Sokal, Durham, NC (US); Carol L. Joanis, Raleigh, NC (US); George A. M. Butterworth, Pittsboro, NC (US); James D. Reed, Raleigh, NC (US); Robert A. Johnson, Turnersville, NJ (US)

(73) Assignee: Family Health International, Durham, NC (US)

( * ) Notice: Subject to any disclaimer, the term of this patent is extended or adjusted under 35 U.S.C. 154(b) by 0 days.

(21) Appl. No.: 11/763,085

(22) Filed: Jun. 14, 2007

(65) Prior Publication Data

US 2008/0051740 A1   Feb. 28, 2008

Related U.S. Application Data

(63) Continuation-in-part of application No. 11/454,604, filed on Jun. 16, 2006.

(51) Int. Cl.
- *A61M 31/00* (2006.01)
- *A61F 5/44* (2006.01)
- *A61F 13/15* (2006.01)
- *A61F 13/20* (2006.01)
- *A61F 6/06* (2006.01)
- *A61F 6/14* (2006.01)

(52) U.S. Cl. .............. 604/285; 604/286; 604/385.18; 604/288; 604/93.01; 604/330; 604/364; 424/430; 424/432

(58) Field of Classification Search ......... 604/285, 604/286; 424/430, 432
See application file for complete search history.

(56) References Cited

U.S. PATENT DOCUMENTS

| | | | |
|---|---|---|---|
| 3,340,874 A * | 9/1967 | Burgeni | 604/379 |
| 3,545,439 A | 12/1970 | Duncan | |
| 3,766,921 A * | 10/1973 | Dulle | 604/12 |
| 3,794,024 A * | 2/1974 | Kokx et al. | 604/361 |
| 3,794,029 A * | 2/1974 | Dulle | 604/369 |
| 3,856,013 A * | 12/1974 | Dulle | 604/369 |
| 3,995,634 A | 12/1976 | Drobish | |
| 4,012,496 A | 3/1977 | Schopflin et al. | |
| 4,016,251 A | 4/1977 | Higuchi et al. | |
| 4,108,180 A * | 8/1978 | Moehrle | 604/369 |
| 4,155,991 A | 5/1979 | Schopflin et al. | |
| 4,198,976 A | 4/1980 | Drobish et al. | |
| 4,250,611 A | 2/1981 | Wong | |
| 4,286,587 A | 9/1981 | Wong | |
| 4,286,593 A | 9/1981 | Place et al. | |
| 4,300,544 A | 11/1981 | Rudel | |
| 4,318,407 A * | 3/1982 | Woon | 604/374 |
| 4,326,510 A | 4/1982 | Buckles | |

(Continued)

*Primary Examiner*—Tatyana Zalukaeva
*Assistant Examiner*—Susan Su
(74) *Attorney, Agent, or Firm*—Womble Carlyle Sandridge & Rice, PLLC

(57) ABSTRACT

A vaginal drug delivery system includes a device formed of porous material that holds a flowable therapeutic formulation. The device, preferably in a soft, prewetted state, is inserted into the vagina to reside typically at or near the cervix where it continuously releases the flowable therapeutic formulation through its outer surface which is in contact with the vaginal surfaces. In operation, the flowable therapeutic formulation migrates via capillary forces from a reservoir that is centrally located in the device and through a covering that envelopes the reservoir.

16 Claims, 15 Drawing Sheets

U.S. PATENT DOCUMENTS

| | | |
|---|---|---|
| 4,526,578 A | 7/1985 | Wong |
| 4,895,170 A | 1/1990 | Tlapek et al. |
| 5,105,827 A | 4/1992 | Augros |
| 5,231,992 A * | 8/1993 | Leon .......................... 600/572 |
| 5,515,862 A * | 5/1996 | Artsi et al. .................. 128/830 |
| 6,302,861 B2 * | 10/2001 | Tweddell et al. .............. 604/15 |
| 6,416,779 B1 * | 7/2002 | D'Augustine et al. ....... 424/430 |
| 6,932,805 B2 * | 8/2005 | Kollwitz et al. ......... 604/385.18 |
| 2001/0014784 A1 * | 8/2001 | Tweddell et al. ............... 604/15 |
| 2002/0107497 A1 * | 8/2002 | Osborn et al. .......... 604/385.18 |
| 2003/0005937 A1 | 1/2003 | Moench et al. |
| 2004/0158222 A1 * | 8/2004 | Mizutani et al. ....... 604/385.17 |
| 2008/0131493 A1 * | 6/2008 | Matloub ..................... 424/449 |

* cited by examiner

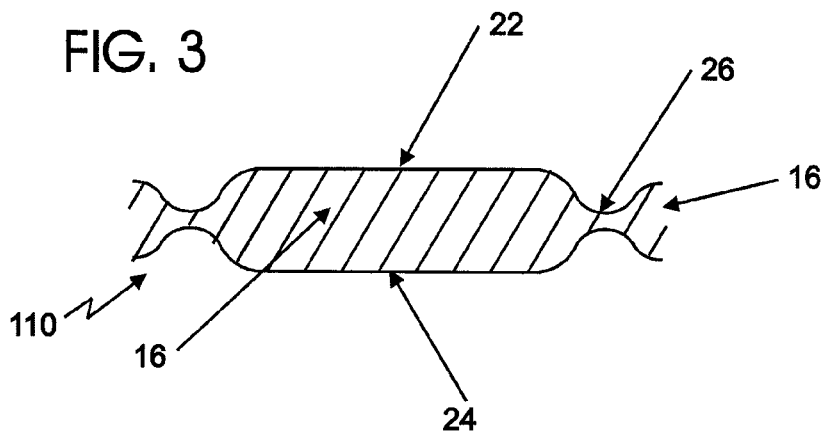
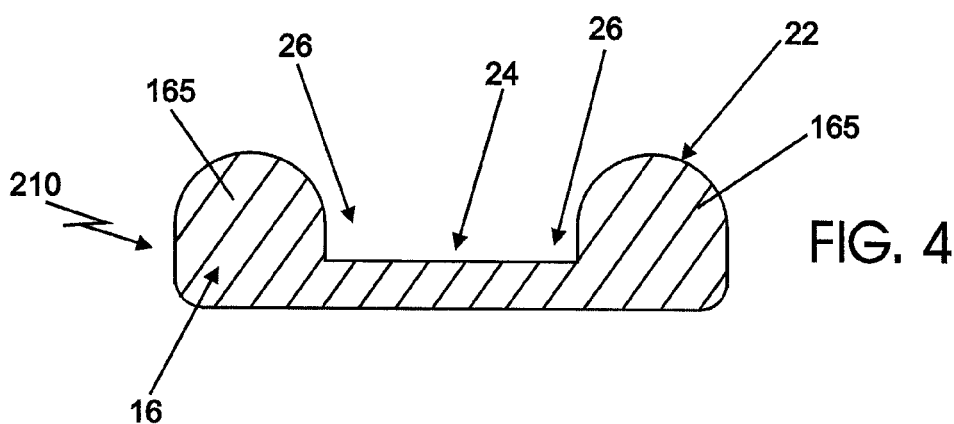
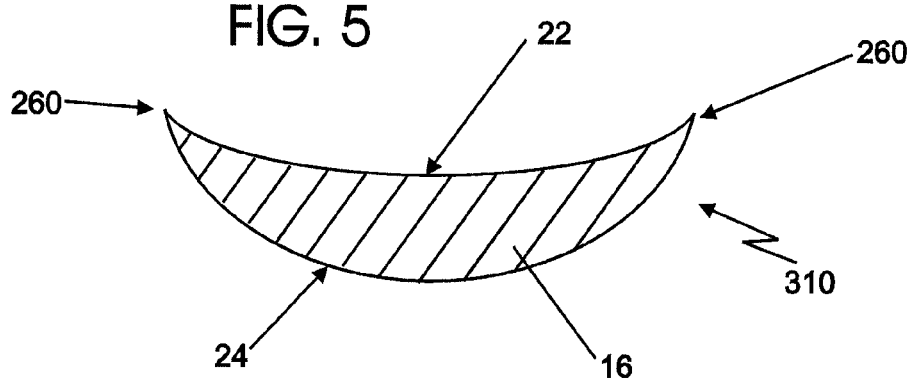

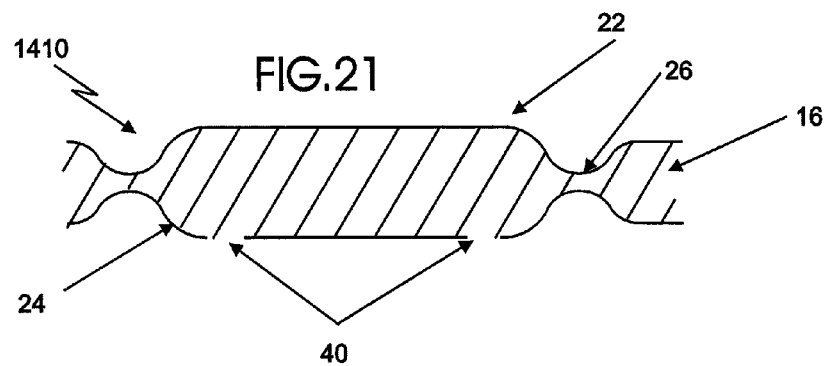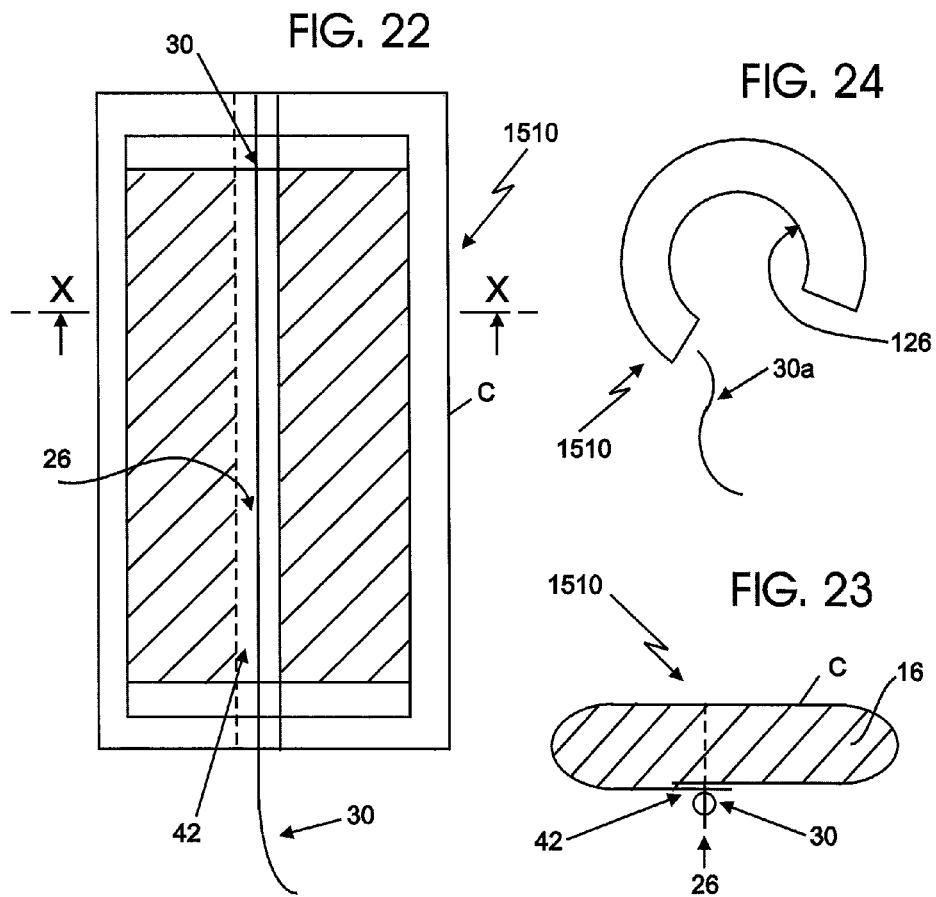

US 7,824,383 B2

VAGINAL DRUG DELIVERY SYSTEM AND METHOD

RELATED APPLICATIONS

This is a continuation-in-part of application Ser. No. 11/454,604, filed Jun. 16, 2006, the content of which is incorporated herein in its entirety.

GOVERNMENT LICENSE RIGHTS

The invention claimed herein was made under U.S. Agency for International Development, Cooperative Agreements #: CCP-A-00-95-00022-02 and GPO-A-00-05-00022-00, and the U.S. government has certain rights therein.

FIELD OF THE INVENTION

The invention relates to the delivery of therapeutic formulations to human females onto or through the vaginal surfaces. More particularly, the invention relates to drug delivery systems that include a device which is inserted into the vagina of a human female to reside typically at or near the cervix, and wherein the device contains and dispenses a flowable therapeutic or prophylactic formulation.

BACKGROUND OF THE INVENTION

There is an urgent need for more simple, inexpensive and acceptable methods for prevention of the human immunodeficiency virus (HIV) in addition to the latex condom. One approach that is being explored is the development of vaginal microbicides that can prevent infection with HIV when administered vaginally prior to or immediately after intercourse. While a number of pharmaceutical agents and formulations are being developed, there is a need for new and improved delivery methods so that as many women as possible will be able to find an acceptable product.

Currently the two main approaches that are used for vaginal delivery of microbicidal formulations are: (1) insertion of the formulation into the vagina with a piston-type tubular device, and (2) applying the formulation onto a diaphragm and then inserting the diaphragm into the vagina. However, many women experience leakage of a gel from the vagina, and consider vaginal gels to be messy, reducing their acceptability. Some women also may not be confident of their ability to properly place a diaphragm over the uterine cervix, and applying a gel onto a diaphragm prior to insertion may be considered inconvenient by some women.

SUMMARY OF THE INVENTION

The present invention overcomes the drawbacks of the prior art by providing a safe, reliable, inexpensive, and easy-to-use drug delivery system and method that can be utilized (1) for the prevention of diseases such as HIV and other sexually transmitted infections that may be introduced through the vagina, (2) for the prevention of pregnancy, and (3) for the treatment of other diseases. In some embodiments, the invention's delivery system includes a soft, single or multilayer device charged with a flowable therapeutic formulation. By "charged," we mean that the flowable therapeutic formulation is put into or onto the device so that the device will become thoroughly saturated with the formulation. This device can be inserted into the vagina, preferably by digital placement, as described below, and will release a flowable therapeutic formulation through its outer surface, which is in contact with the vaginal surfaces.

In certain embodiments, the device of the present invention may have a low density prior to being loaded/charged with a therapeutic formulation. It is soft, pliable, and the outer surface is saturated with the contained, flowable therapeutic formulation, making the device easy to insert with minimal friction and resistance. Consequently, in its primary applications, the device can be used menstrually and intra-menstrually without being affected by either the dry or moist state of the vaginal tissues. The device also may be easily packaged in a non-compressed state, for example, in a watertight package. Also, in some embodiments, the device may be disposable and/or biodegradable.

While some less costly embodiments of the invention are insertable into the vagina by the user's finger, the device may also be designed for insertion using an inserter, such as a piston-type vaginal applicator similar to those used for tampons. Alternatively, the device may be constructed with a pocket dimensioned for a user's finger to aid in properly inserting the device with a finger.

In some embodiments, the device of the invention includes a reservoir that contains the flowable therapeutic formulation. The reservoir releases the flowable therapeutic formulation when the device is in use. The reservoir also may be partially or completely enveloped by an optional covering.

The reservoir and covering, if applied, are both made of textile materials, and their physical characteristics are chosen to assist in forcing the flowable therapeutic formulation from the reservoir. This is achieved via flow from capillary spaces or pores in the material of the reservoir, into and through the surrounding covering, to the outer or external surface of the device, and finally to the vaginal surfaces.

The devices of the invention described herein also may include a securely attached withdrawal cord of suitable material, for example, a textile or plastic material. The device may also include appendages affixed to or formed with the perimeter or external surface of the device to facilitate its removal.

The flowable therapeutic formulation may be prepared using a wide variety of thickeners or other excipients, resulting in a wide variety of physical and chemical characteristics, which are known to those with expertise in the art of preparing pharmaceutical formulations.

The therapeutic agents included in the formulation may be selected from the group of hormonal and non-hormonal contraceptive agents, vaginal spermicides, vaginal microbicides, antibacterial agents, antifungal agents, antiviral agents, anti-HIV agents, anticancer agents, and combinations thereof. A tabulation of vaginal microbicides, whose use is contemplated by this new device, is contained, for example, in *Microbicide Quarterly*, Volume 2, Number 1, January through March of 2004 and in the journal article, "Microbicides: A new frontier in HIV prevention," by Ian McGowan, *Biologicals* Vol. 34 (2006), pp 241-255.

With respect to the prevention of HIV and sexually transmitted infections (STI's), the release of a flowable therapeutic formulation into the vagina is intended to provide an agent that will coat and/or be absorbed by vaginal tissues in order to inactivate infectious agents or prevent their contact with susceptible tissues or cells.

In general, the pores formed in the reservoir, in the one or more layers surrounding it, and in the external surface of the covering, are such that even in the absence of any external pressure, the flowable therapeutic formulation will naturally migrate outwardly from the reservoir to the outermost surface of the device. This migration is driven primarily by the capillary forces resulting from interaction of the flowable therapeutic formulation with the structural surfaces of the reservoir, covering material, and the dimensions of the pores within them. The migration can be controlled by manipulating the various factors that influence the capillary forces, including but not limited to: (a) the dimensions of the interconnected pores in the reservoir and in the enveloping covering; (b) the contact angle between the flowable therapeutic formulation and the structural surfaces of the reservoir and cover material; and c) the viscosity and other physico-chemical characteristics of the therapeutic formulation. With the appropriate choice of materials and therapeutic formulation characteristics, the flowable therapeutic formulation will naturally migrate to the outermost pores of the covering of the device. In doing so, the available flowable therapeutic formulation within the total device will continue to accumulate at the outermost surface of the device from which it can lubricate the device during insertion.

Following insertion, the device will continue to transfer flowable therapeutic formulation to the vaginal surfaces. As the outside surface of the device is depleted of flowable therapeutic formulation, it is replenished by the continued migration of flowable therapeutic formulation from the reservoir to the outermost pores of the enveloping covering. Additionally, the movement or migration of flowable formulation may be augmented by intermittent compression of the device by variations in the physiologic forces acting on the pelvis and vagina caused by activities such as breathing, coughing, standing, walking, sitting, urinating and sexual intercourse.

In one manner of carrying out the invention, the device, in a therapeutically-filled and surface pre-wetted, uncompressed state, does not adhere to dry, unmoistened vaginal tissue. This is a particularly desirable feature for use of the device during non-menstruating days of the menstrual cycle, in order to avoid damage to vaginal surfaces which can occur when a dry, absorbent device such as a tampon is put in contact with unmoistened vaginal tissues. As is known in the art, a dry tampon can stick to the epithelial surfaces of the vaginal walls, and cause epithelial denudation when it is removed. In the embodiments described herein, this invention avoids that danger.

While certain embodiments of the invention, as described above, take advantage of differential capillary forces between the reservoir and covering in the delivery of a therapeutic formulation to vaginal surfaces, other embodiments of the invention may be made that rely significantly on the physiologic forces acting on the device. In this case the size of the pores or other structural features in the outer layer(s) control the rate of the flow of the therapeutic formulation from the reservoir onto vaginal surfaces. However, the design of such an embodiment would take into account the capillary forces of the materials and their interfaces, so as not to unduly inhibit or accelerate the delivery of the therapeutic formulation. In addition, it is desirable that embodiments that rely significantly on physiologic forces and resultant physical compression of the device for extrusion of the flowable formulation preferably use materials such that the capillary forces of the device components resist re-absorption of the therapeutic formulation back into the device.

The inventors have also found that there may be certain occasions where a slower release of therapeutic formulation is desired. This slow release is accomplished, in certain embodiments, by careful selection of the outer or intermediate covers. For example, the outer cover (or an intermediate cover, as shown in FIG. 34) may be composed of:

a dense non-woven material with small pores and fiber surface characteristics which together reduce the speed of flow out of the device; or a partially occlusive layer such as a film with fewer or smaller apertures; or an outer coating designed to dissolve only in the presence of moisture and/or body heat and/or at a specific pH level and/or in the presence of chemicals that are found in the vagina.

Also, slow release may be obtained by designing the device so that the magnitude of the capillary forces that force the flowable therapeutic formulation from the reservoir to the surface may be reduced, compared to the capillary forces that would be used for a more rapid release.

For various reasons known to those skilled in the arts, such as the stability of a particular active ingredient or the shipping weight of large numbers of devices, it may be advantageous to package the device with a soluble or dispersible flowable material in dry form which is activatable by the user by adding a liquid such as water, vinegar or mineral oil before insertion into the vagina. Some active agents are more stable in a dry or powder form than when dissolved in a liquid. Some formulations could be applied to the device in dry form, or applied in wet form and then lyophilized, so that the user could add liquid to the device before insertion. Since each device can hold 10 ml of fluid or more, it might be commercially advantageous to produce the device in a dry state, to minimize shipping charges. Depending on the particular therapeutic formulation, it could be appropriate to add water, or an acidic solution such as vinegar, or a lipid solution such as mineral oil, in order to prepare the device for insertion.

In another embodiment of the invention, the size of the finger pocket is enlarged and adapted to the size of the tip of a man's penis. For this embodiment, the device is put on the tip of the penis, and inserted into the vagina at the beginning of sexual intercourse. In one embodiment, the device is designed to remain in the vagina after the first penile insertion. In this embodiment, the pocket will cover less of the penis than a condom, and will fit more loosely on the penis than a condom. Thus the frictional forces of the vaginal walls should retain the device in the upper vagina, near the cervix, following the first penile insertion of the sexual intercourse. The inner surface of the finger pocket of this embodiment may be more slippery than the outer surface in order to ensure that the device slides off the penis following the first penile insertion.

BRIEF DESCRIPTION OF THE DRAWINGS

FIGS. 3 through 5 are sectional views, similar to FIG. 2, showing alternative embodiments.

FIGS. 18 through 21 illustrate alternative embodiments which permit easy grasping of the device for insertion and removal.

FIG. 22 is a plan view of an elongated form of the device and which can be used to surround the cervix or be positioned generally parallel to the vaginal axis.

FIG. 23 is a sectional view of the device of FIG. 22 taken at line X-X.

FIG. 24 shows the device of FIGS. 22 and 23 formed to be inserted to surround the cervix.

DETAILED DESCRIPTION OF THE INVENTION

Certain exemplary embodiments of the present invention are described below and illustrated in the attached Figures. The embodiments described are only for purposes of illustrating the present invention and should not be interpreted as limiting the scope of the invention, which, of course, is limited only by the claims below. Other embodiments of the invention, and certain modifications and improvements of the described embodiments, will occur to those skilled in the art, and all such alternate embodiments, modifications and improvements are within the scope of the present invention.

Definitions:
1. A "therapeutic agent" refers to an active ingredient in a therapeutic formulation. A therapeutic agent may provide one or more medical benefits to a woman, including, but not limited to:
   a. the prevention of various diseases especially sexually transmitted infections,
   b. the prevention of pregnancy, i.e., contraceptive effects, and
   c. the treatment of various diseases.
2. A "therapeutic formulation" is a pharmaceutical formulation that includes one or more therapeutic agents. In addition to a therapeutic agent, a therapeutic formulation may include thickening agents, lubricants, pH buffering agents and other excipients that are familiar to those skilled in the art of pharmaceutical formulations.
3. The term "flowable therapeutic formulation" refers to a therapeutic formulation that is capable of running, flowing, percolating or wicking within and between porous media and for which the liquid may consist of one or more phases, with the predominant phase being either aqueous or oily in nature. Flowable therapeutic formulations may be of low or high viscosity and the viscosity may be dependent or independent of shear rate.
4. "Vaginal surfaces" refers to the vaginal walls and other surfaces that would be in contact with a flowable formulation placed in the vagina. These surfaces include the cervix, the vaginal walls, the vaginal fornices, and the vulva.
5. The term "capillary forces" or "capillary suction forces" is used to denote the forces resulting from the complex interaction of flowable materials, their surface tension, surface contact angles of wetting, and pore sizes that influence the interaction of fibrous or other similar porous materials with flowable liquids.
6. The term "physiologic forces" refers to the forces that may exert pressure on a device of this invention when the device is in the vagina, including, but not limited to, differences in pelvic or vaginal pressure caused by breathing, standing, walking, sitting, urinating or having sexual intercourse.

Figure 1:
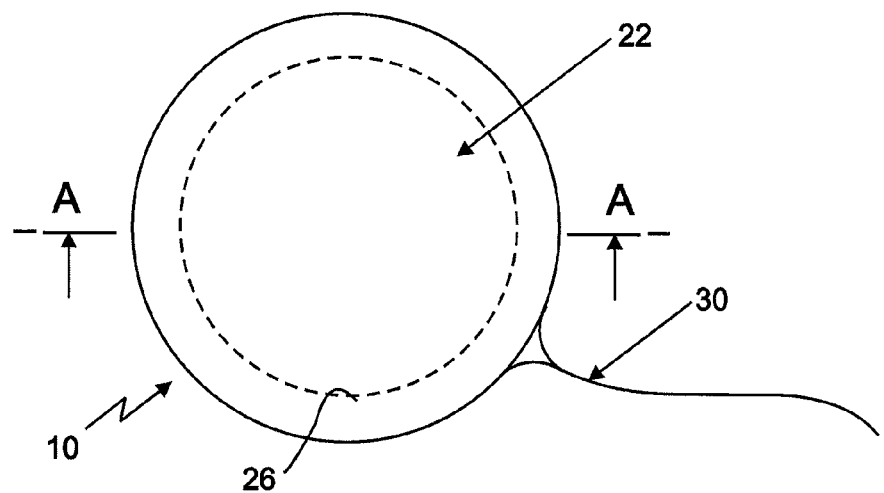
FIG. 1 is a plan view of one vaginally inserted drug delivery device of the invention. The body of the device is flat and has a symmetrical circular shape.
Figure 2:
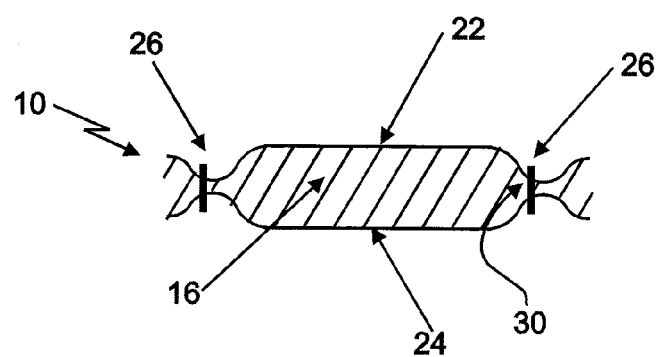
FIG. 2 is a sectional view of the device of FIG. 1, taken substantially at line A-A.

Referring to the drawings, and particularly to FIGS. 1 and 2, there is shown one embodiment of an insertable device 10 constructed in accordance with the present invention. As mentioned above, device 10 may be a disposable device that is charged with therapeutic agent(s) contained within a flowable therapeutic formulation and is suitable for insertion into the vaginal cavity to reside typically at or near the cervix.

Figure 6:
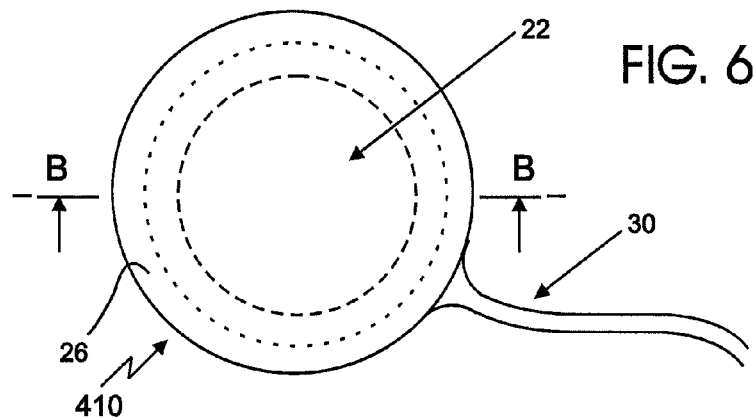
FIG. 6 is a plan view of an alternative embodiment having a free-floating reservoir.
Figure 7:
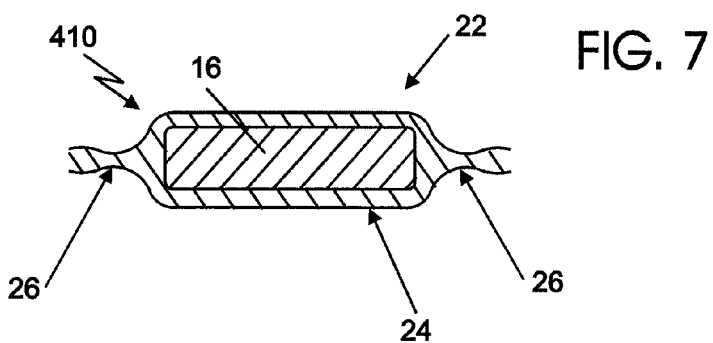
FIG. 7 is a sectional view of the device of FIG. 6, taken substantially at line B-B.

Device 10 has a generally flat, circular configuration and includes a reservoir 16 and an enclosing covering comprising top and bottom covers 22 and 24, respectively. The boundaries of reservoir 16 are generally coterminous with the boundaries of top and bottom covers 22 and 24. The reservoir 16 and covers 22, 24 of device 10 are secured together by a circular seal 26. Seal 26 may take the form of stitching, gluing, heat sealing or other suitable form. It may extend through the periphery of the composite structure, as shown in FIGS. 1 and 2, or only through covers 22, 24 as shown in FIGS. 6 and 7. Seal 26 may be set inwards from, near, or coterminous with the perimeter edge. When it is desired to include a withdrawal cord as a part of device 10, for ease in manufacture the cord (for example, withdrawal cord 30, FIG. 1) may be incorporated into the device in the same operation that forms the seal.

The materials used for the top and bottom covers 22, 24 may be identical, similar, or different. For example, the material of cover 22 may be permeable to the flowable therapeutic formulation and the material of cover 24 can be less or more permeable than cover 22. In other embodiments, cover 24 may be impermeable to flowable therapeutic formulation, permitting device 10 to discharge flowable therapeutic formulation through only one surface; i.e., the outside surface of cover 22.

The cross-sectional views of FIGS. 3, 4 and 5 illustrate several possibilities for device configurations and perimeter sealing. In FIG. 3, seal 26 of device 110 is achieved by a combination of heat and pressure as an intermittent or continuous seal. FIG. 4 illustrates an asymmetric shaping of device 210 to permit intimate cervical contact, using a ring-shaped reservoir 16 over-wrapped around the perimeter seal with cover 22 and sealed to cover 24 inwardly of the reservoir profile 165. Referring to FIG. 5, the perimeter and the sealing of device 310 are contiguous and coterminous at 260. This configuration may be achieved by a heat or pressure sealing process.

Referring now to FIGS. 6 and 7, another device 410 is shown wherein the reservoir 16 is not physically attached to the top and bottom covers 22 and 24. This free-floating reservoir 16 is in contact with the inner surfaces of covers 22 and 24 but is not secured at the seal 26 joining top 22 and bottom 24 covers. Varying the formation of the periphery of the device, by including or excluding component layers in joining cover 22 to cover 24, is one means to control the softness of the peripheral edge and the flexibility of the entire device.

Figure 8:
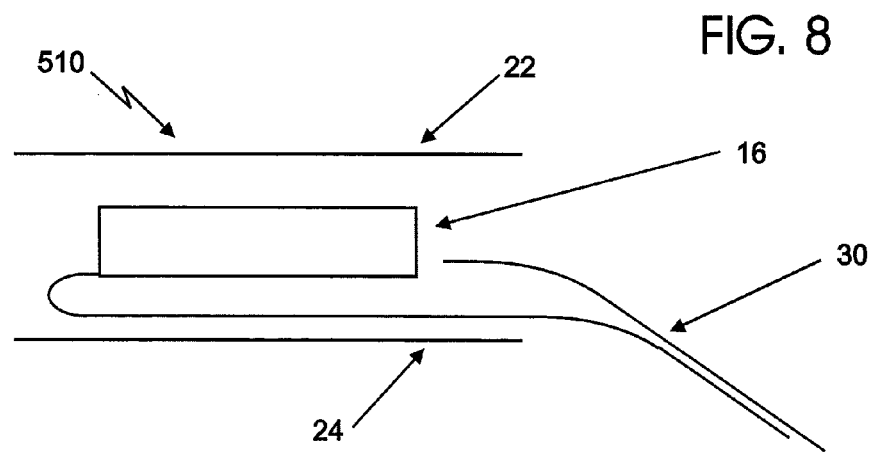
FIG. 8 is a sectional view of a further alternative embodiment incorporating a removal cord.

FIGS. 8 through 11 show the use of differently shaped covers 22 and 24. FIG. 8 illustrates an exploded view of device 510 with a juxtaposition of covers 22 and 24 and reservoir 16, together with a withdrawal cord 30.

Figure 9:
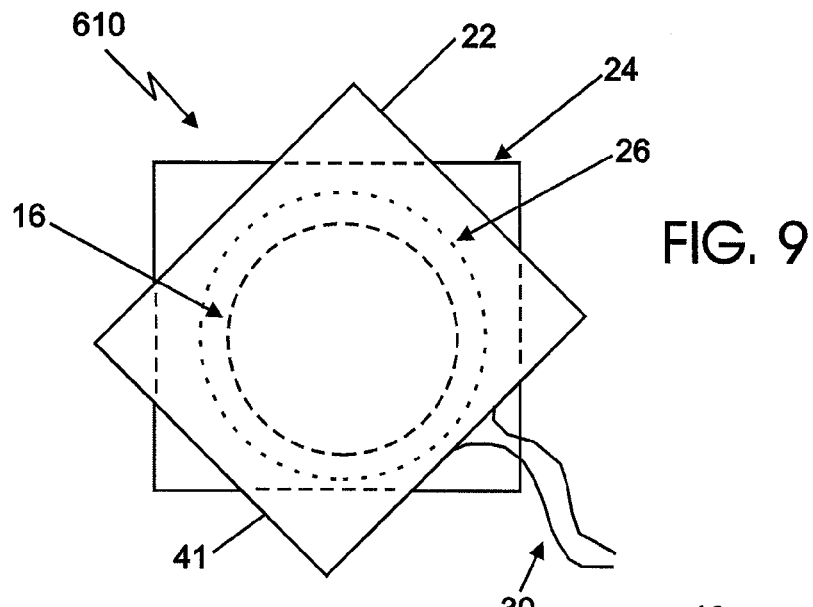
FIGS. 9 through 11 show, in plan, alternative embodiments with differently shaped coverings for achieving various advantages, including easier grasping of the device for insertion or removal.

FIG. 9 shows a device 610 in which covers 22 and 24 are square, with one cover offset by an angle of approximately 45° relative to the other before covers 22 and 24 are sealed together to envelope the reservoir. This leaves eight flanges/appendages 41 with free corner-shaped edges.

Figure 10:
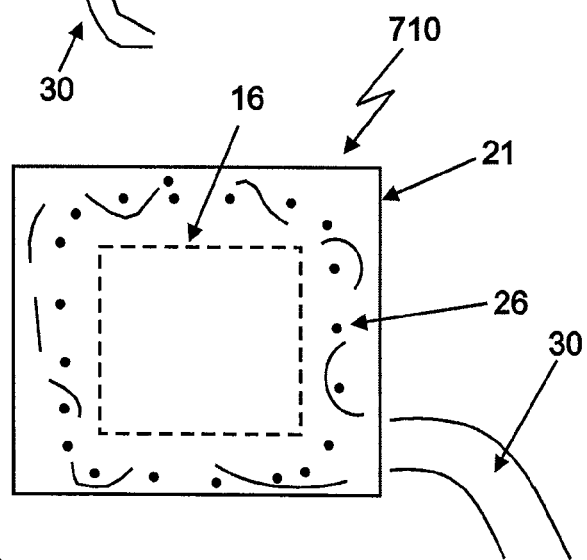

FIG. 10 shows another device 710 with square covers 22 and 24, but with essentially no offset and with the cover perimeters coterminous.

Figure 11:
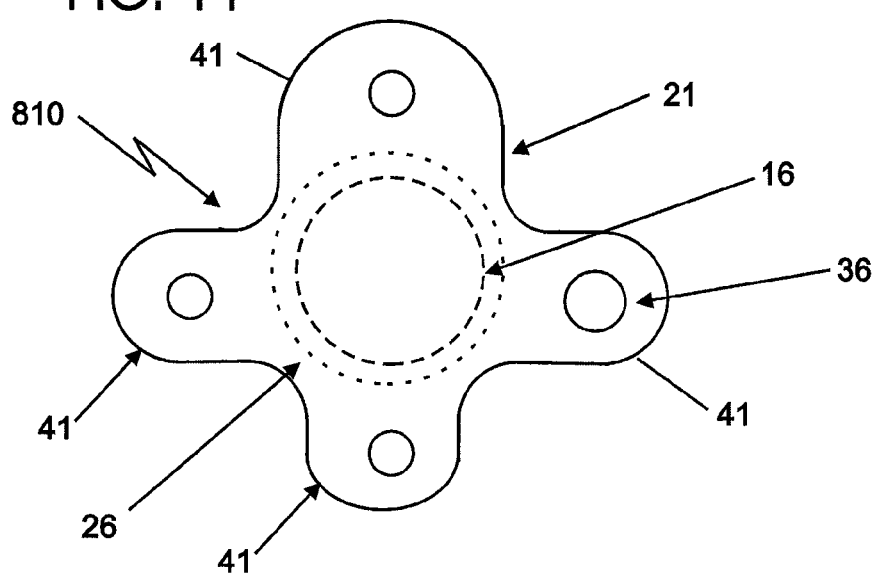

FIG. 11 illustrates another device 810 with flexible appendages 41 in the form of a four-petal flower design. The user's ability to grasp the petals may be augmented by the addition of grasping holes 36 punched through the extended petal/flanges 41 of either or both covers 22 and 24. The number of appendages or petals may, of course, be fewer or greater than four.

Figure 12:
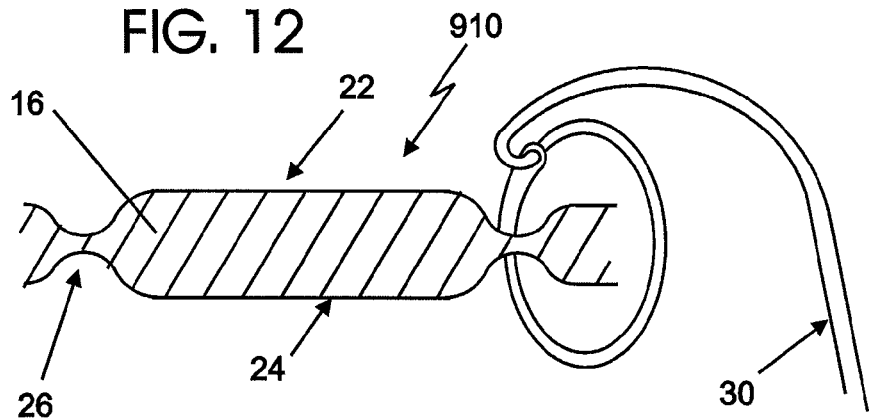
FIG. 12 depicts a device with another type of attachment for the withdrawal cord.

As described above, a withdrawal cord, if required, may be attached to the device in numerous ways. Another attachment technique is shown in FIG. 12. The withdrawal cord 30 has been formed from a loop of cord pushed through the device near the edge. In this embodiment, the cord penetrates the device proximate the seal 26. This method of attachment is commonly known as a Prussic knot, and may be used with any of the embodiments described herein. With this or other embodiments, the cord could also penetrate the device outside the boundaries of the seal 26. The two free ends of the cord are preferably tied in a simple knot such as a granny knot or a square knot (not shown). This allows a female two additional methods to grasp the removal cord: (1) she could grasp the knot at the end, or (2) she could pull on the loop between the two cords. Depending on consumer preference, the cord may be made with varying colors and/or opacity characteristics, e.g., opaque white or colorless and transparent.

Figure 13:
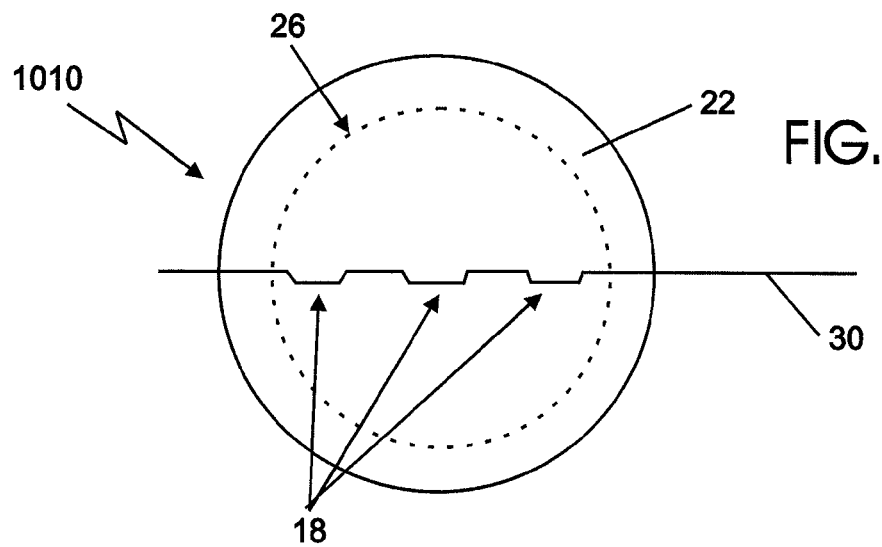
FIGS. 13 and 14 illustrate a device with a simplification of the withdrawal cord attachment suited to automated device manufacture.
Figure 14:
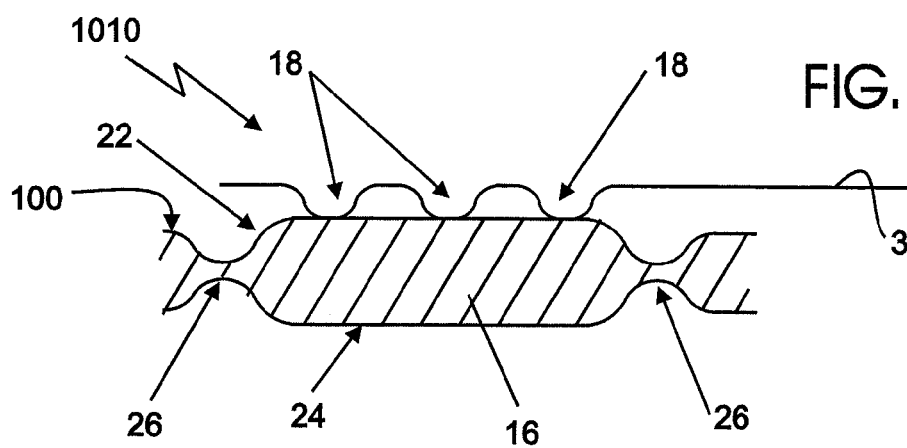

FIGS. 13 and 14 illustrate a device 1010 with a single withdrawal cord 30 that has been bonded to one of the device covers 22 with a series of adhesive seals 18, using cold glue, hot melt glue, thermal or ultrasonic bonding.

Figure 15:
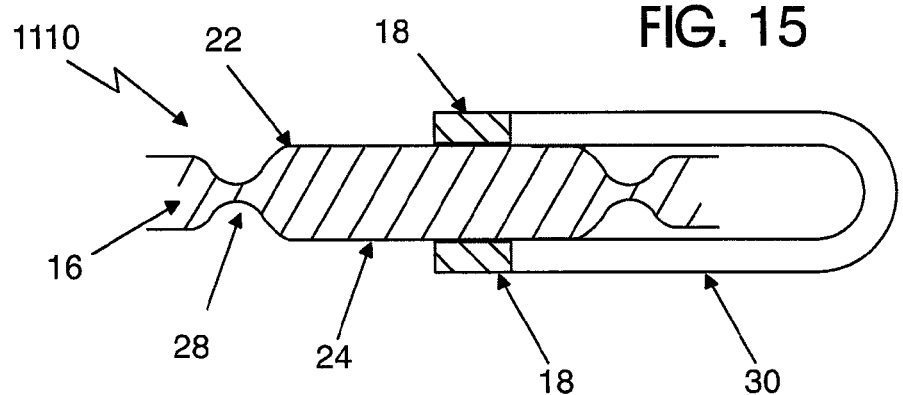
FIG. 15 illustrates another withdrawal cord attachment technique.

In another embodiment, shown in FIG. 15, the withdrawal cord 30 of device 1110 includes a single loop, one end of which is affixed to the surface of cover 22 with the other end affixed to the surface of cover 24 at bonding points 18. The cord 30 could be made of various materials, including an opaque white textile material or a transparent plastic film.

Figure 16A:
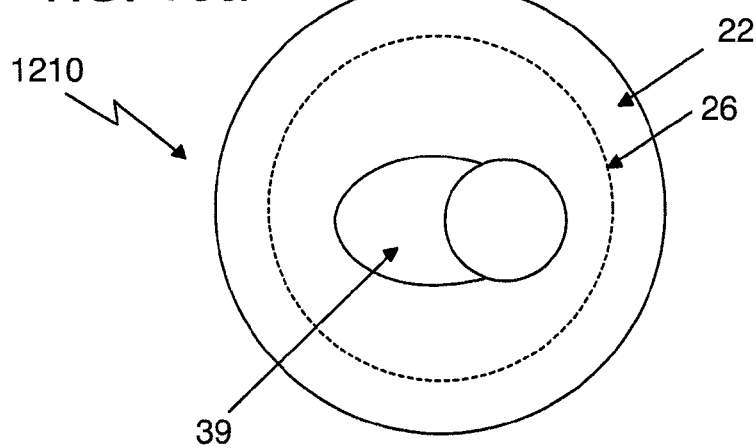
FIGS. 16a through 17b illustrate embodiments that include a pocket for insertion.
Figure 16B:
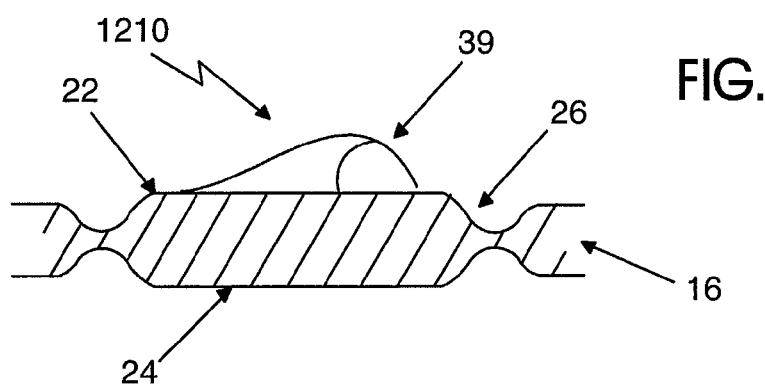

FIGS. 16(*a*) and 16(*b*) illustrate another embodiment of the device 1210 that includes a finger pocket 39 attached to the top cover 22 inside the seal 26. Finger pocket 39 permits the user to support device 1210 during insertion and to position the device at or near the cervix. It should be noted that the preferred structure of device 1210 is one where the pocket is attached to one cover 22 leaving the other cover 24 free of obstructions and able to make intimate contact with the cervix and surrounding vaginal tissue.

Figure 17A:
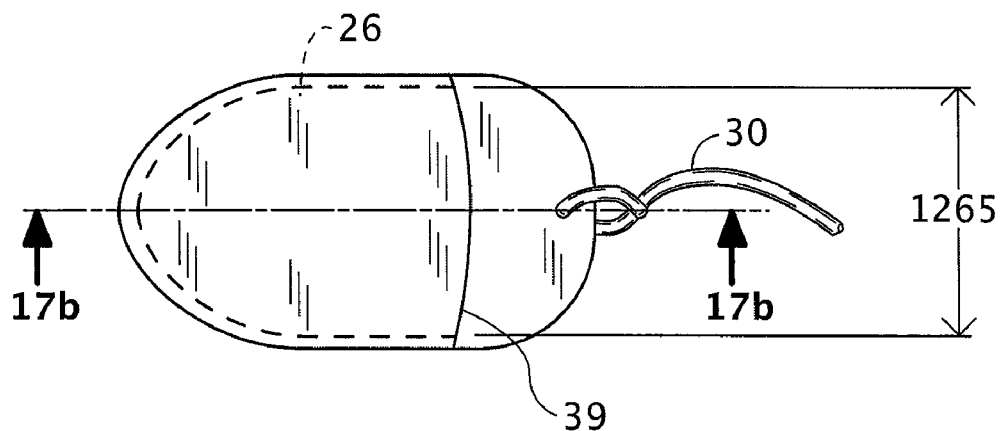
Figure 17B:
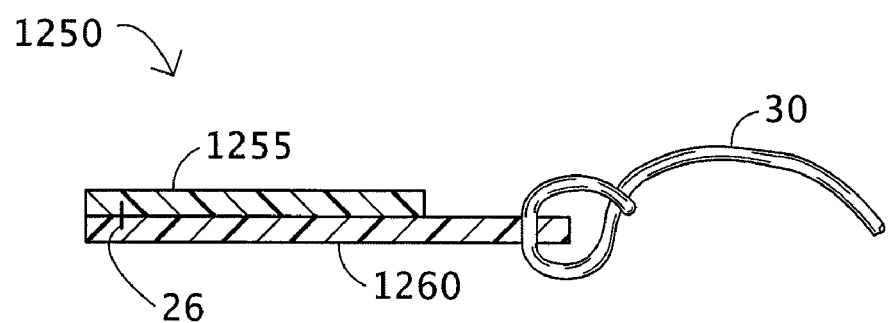

FIGS. 17(*a*) and 17(*b*) show yet another embodiment of the device 1250 in which the finger pocket 39 is constructed by seal 26 connecting two layers of material 1255 and 1260 to enclose a finger pocket 39. In one embodiment, layers 1255 and 1260 may be formed of similar materials or similar multilayer materials. Unlike the previous embodiments, however, the layers 1255 and 1260 are formed of materials selected to actually comprise the reservoir structure without the necessity of other outer covers. In one embodiment, each of the layers may be formed of a felt-like non-woven material having a thickness of about ⅛ inch, although the material and thickness of the material may be selected based on the factors that are described in greater detail below. When formed in this manner, the layers 1255 and 1260 will themselves be charged with and wetted/saturated with the desired therapeutic formulation. Additionally, the inner surfaces of the layers 1255, 1260 may be formed to be smoother, and thus more slippery, so that the device may easily slip off of the insertion device after initial insertion and placement. An example of a non-woven material that could provide a slippery inner surface is made by Delstar Technologies Inc., Philadelphia, Pa., and marketed as item 30SR-Delnet/3.7NPET-E. This material is a composite non-woven fabric with a slippery, non-adherent layer on one side, and is similar to non-woven composites that are used in wound dressings and bandages. The width of the finger pocket, shown as dimension 1265, may be varied depending on the method of insertion, as also described in greater detail below. The contour and openness of the finger pocket may also be varied to facilitate insertion by a finger or other insertion device; i.e., layer 1255 may be dimensioned such that the pocket 39 will receive a finger, or as described below, a penis.

In another embodiment, the shape of the finger pocket may be panduriform, i.e., violin-shaped with a slight narrowing of the sides of the pocket near the pocket opening. This improves the friction between the sides of the user's finger and the sides of the finger pocket to facilitate insertion of the device.

This device also has a removal cord 30 attached to the device with a Prussic knot, similar to FIG. 12, and a terminal knot (not shown). The length of the cord 30 from the edge of the device to the terminal knot 51 should be between about 10 cm, the length commonly used for a tampon, and 25 cm.

Figure 18:
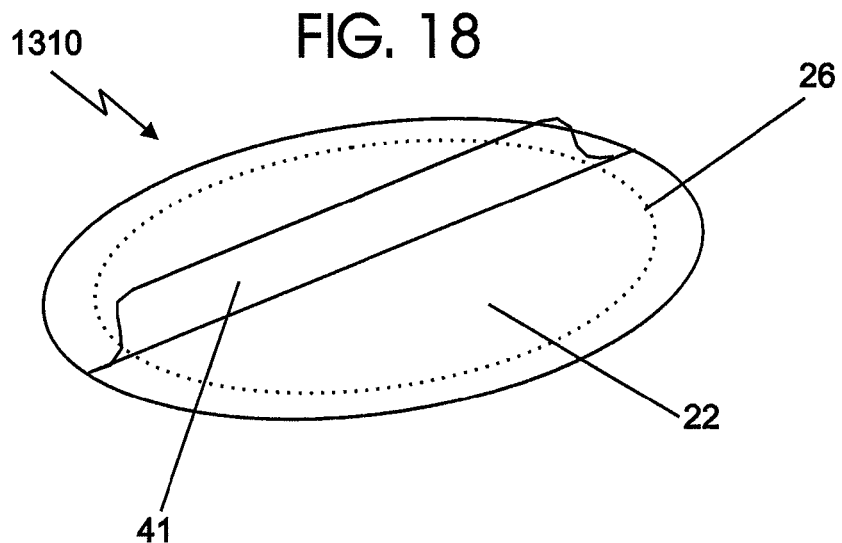
Figure 19:
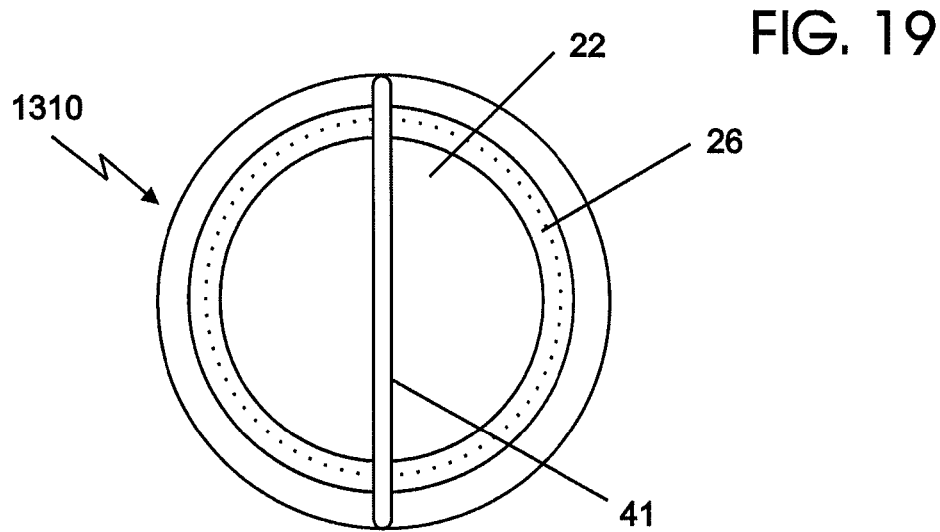
Figure 20:
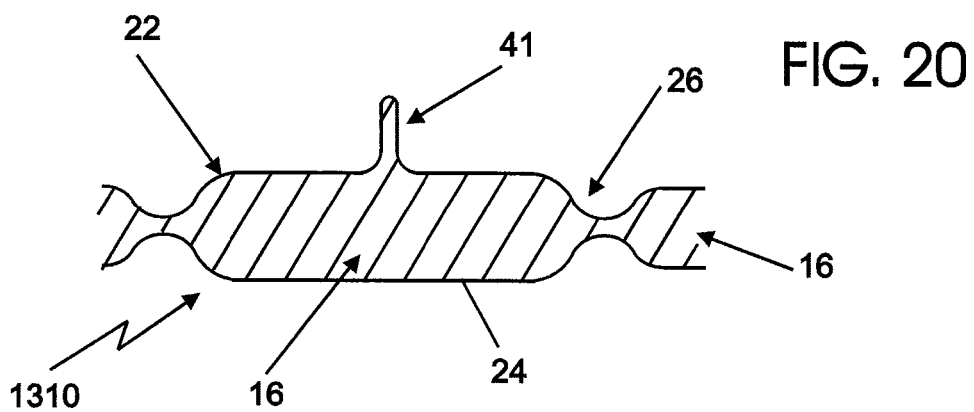
Figure 26:
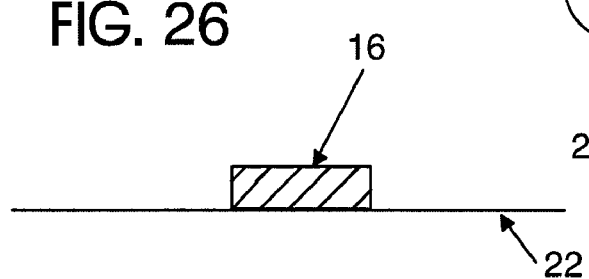
FIGS. 25 through 29 show an alternative form of the device construction providing an asymmetric cross-section intended to concentrate flowable therapeutic formulation release from one side of the device.

FIGS. 18 through 20 illustrate another device 1310 including a grasping flange 41 that is constructed from a pleat of the material forming cover 22 before the device 1310 is sealed, with a sealing line 26 joining covers 22 and 24 to envelope reservoir 16.

FIG. 21 illustrates a device 1410 with a less expensive and simpler grasping structure, in which two finger slits 40 have been created in the bottom cover 24. Slits 40 permit the user to grasp the device in a pinch grip between finger and thumb to initiate insertion, followed by a single finger engaged in one slit 40 to complete insertion and positioning. The covering may be spot sealed to the reservoir between the two slits (not shown), or the device may be manufactured without any special attachment near the slits.

While the embodiments described above are intended for self insertion by the user, there may be occasions when a physician would use the device to deliver a medication in a specific area of the vagina, for example, after a surgical procedure. In such cases, the device may be configured to cover the length of the vagina or alternatively, may be configured to restrict dispensing of therapeutic formulation to regions surrounding the cervix, rather than covering it. FIGS. 22 through 24 illustrate such an elongated device 1510, which, for human use, may be about two to four inches in length and about one half to one inch in width. Device 1510 includes a compressible reservoir 16 that is wrapped with a covering C formed of a single sheet of material that is overlapped at 42 and sealed together. The sealing may optionally include a withdrawal cord 30 at the sealing line 26. The sealing line may be sewn through the reservoir of the device at 26 or may simply be confined to the surface at the covering overlap 42. In use, elongated device 1510, charged with the requisite flowable therapeutic formulation, may be positioned and shaped by a physician or nurse during insertion to ensure dispensing of flowable therapeutic formulation to specific regions of the vagina such as around the cervix or in the fornices. In a device designed to surround the cervix, inclusion of a tensioned strip of elastic material, e.g., LYCRA® material, incorporated in the overlap 42 may be used to cause the completed device to bias towards a curved or arcuate configuration similar to that shown in FIG. 24. The embodiment shown in FIGS. 22-24 would also lend itself to self-insertion by women with the use of a cylindrical inserter device such as those typically used with tampons.

Figure 25:
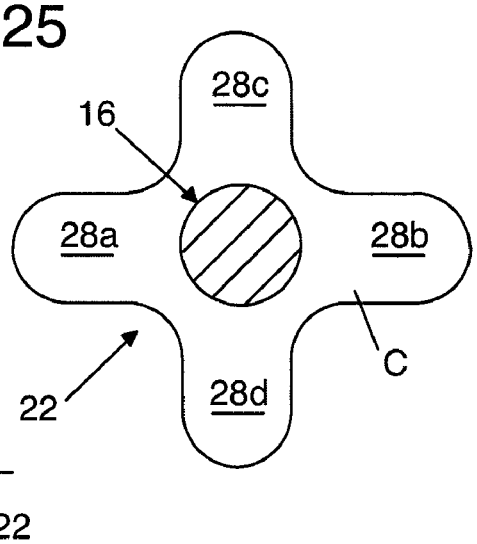
Figure 27:
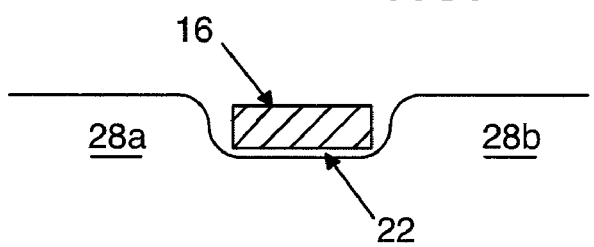
Figure 28:
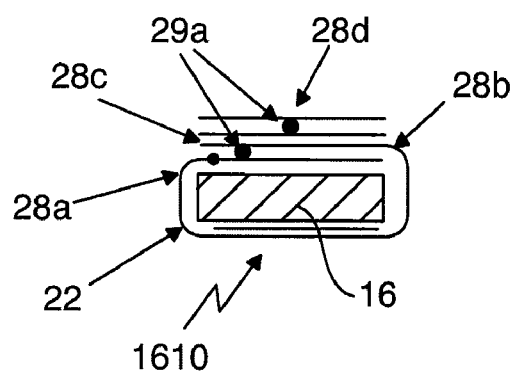
Figure 29:
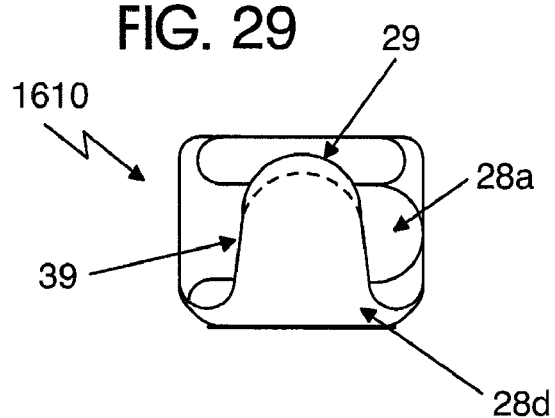
Figure 30:
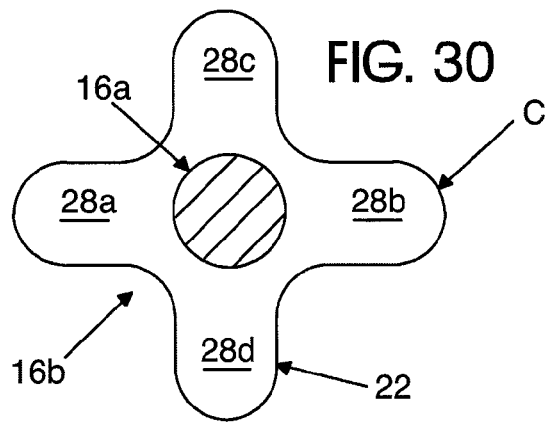
FIGS. 30 through 33 show a device with an adaptation of the constructions shown in FIGS. 1-5 and 25-29, in which similar or different reservoirs may be employed to control flowable-material release.
Figure 31:
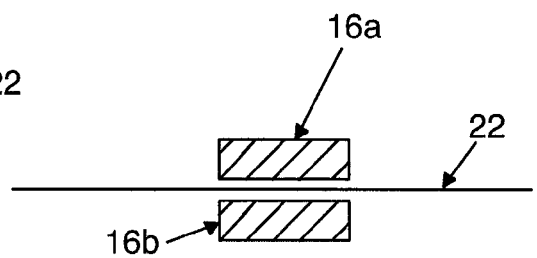
Figure 32:
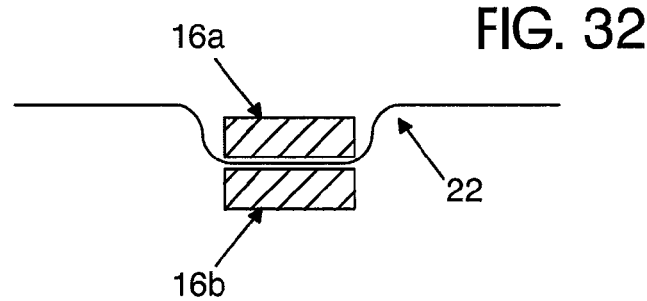
Figure 33:
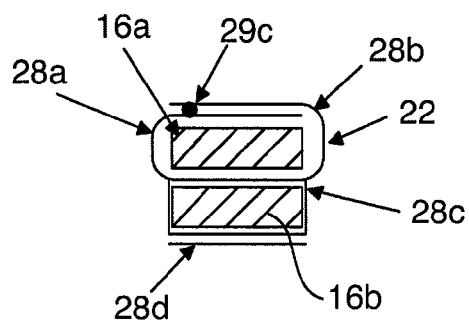

FIGS. 25 through 29 show a device 1610 having a covering C formed of a single sheet of material die cut to a shape such that when it is folded as shown to envelope the reservoir 16, any bulk caused by three dimensional folding is minimized. In the illustrated embodiment, a flower-shaped piece of material is die cut with four flaps 28a, 28b, 28c, and 28d (FIG. 25). The reservoir material 16 is centered on the covering 22 FIG. 26), pressed into it (FIG. 27) and flaps 28a and 28b folded in sequence over the reservoir (FIGS. 28 and 29). These flaps are held in place by the folding and sealing of flaps 28c and 28d over flaps 28a and 28b with a bead or drop of a soft melt or cold adhesive/glue. The final sealing of flaps 28c and 28d can be configured to secure all flaps over the reservoir and also create a finger pocket 39 between flaps 28c and 28d. As will be appreciated by those skilled in the art, the number of flaps may be fewer or greater than four.

FIGS. 30 through 33 show a device 1710 incorporating more than one reservoir into the device, in this case, two reservoirs 16a and 16b. Each reservoir may contain the same flowable therapeutic formulation and therapeutic agent, or they may contain different flowable therapeutic formulations, therapeutic agents or reservoir materials 16. The reservoir materials, 16a and 16b, may be bonded or sealed to the cover material 22 before the flaps are folded, i.e. where the surfaces are shown in contact in FIG. 31. The different therapeutic formulations and reservoir materials may be selected for differing release rates. Sealing the flaps 28a and 28b at 29c and the sealing of flaps 28c and 28d at 29d holds the covering over the two reservoirs.

For the embodiments shown in FIGS. 25 through 29 and 30 through 33, the size and shape of the flaps may be configured so that varying amounts of the material forming reservoirs 16 are not covered by separate covering. The reservoir materials 16a, 16b may be bonded or sealed (not shown) to the material 22 before the flaps are folded. Such a structure may be used to provide rapid release of some of the therapeutic formulation at the time of insertion, while retaining the remaining therapeutic formulation for later release. Similarly, while not illustrated, embodiments of the device may be formed with perforations in the covering to provide for rapid release of some of the therapeutic formulation at the time of insertion.

Figure 34:
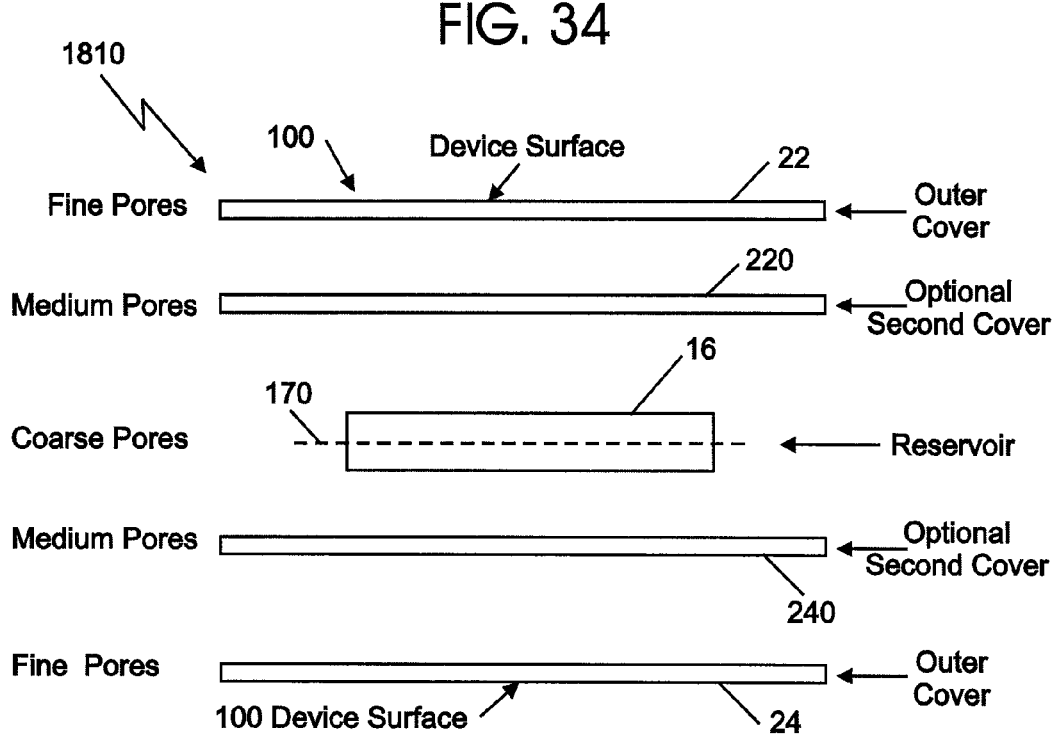
FIG. 34 is an exploded cross-section of an alternative embodiment in which additional cover layers are incorporated above and below the reservoir. The reservoir and layer structures are arranged so that there is a step change in pore size distribution and/or surface wetting characteristics as one moves from the central plane of the reservoir and towards opposite surfaces of the device.

FIG. 34 shows another device 1810 in an exploded sectional view taken through the center of the device. The covering for device 1810 includes two layers on each side of reservoir 16, instead of one. Thus, device 1810 comprises two outer covers 22 and 24, two intermediate covers 220 and 240, and a reservoir 16 symmetrically or asymmetrically located about the mid-plane 170. The surface and porosity characteristics of the reservoir are such that when it is filled with a defined flowable therapeutic formulation, there are relatively low capillary forces causing the flowable therapeutic formulation to be retained by the reservoir. The surface and porosity characteristics of the materials comprising the intermediate covers 220 and 240 possess higher capillary and directional surface tension forces regarding the flowable therapeutic formulation causing it to migrate into them. The outer covers 22 and 24 have surface and porosity characteristics which create an even higher capillary and directional surface tension force on the flowable therapeutic formulation, higher than those of the intermediate cover materials and substantially greater than those of the reservoir. All other things being equal, a discontinuous gradient distribution of average pore sizes, with the reservoir 16 material having coarse pores, the intermediate cover 220, 240 materials having medium pores, and the cover materials 22, 24 having fine pores, as shown in FIG. 34, is one way to cause flowable therapeutic formulation to migrate under the action of capillary forces from the reservoir to the outermost surface of the device at 100. This establishes a gradient of capillary forces whereby the contained flowable therapeutic formulation is driven continuously to each outer surface until that surface is saturated with flowable therapeutic formulation and the flow dynamics attain equilibrium. The use of one or more intermediate layers may be particularly desirable if a slow release of the therapeutic formulation is desired.

Figure 35:
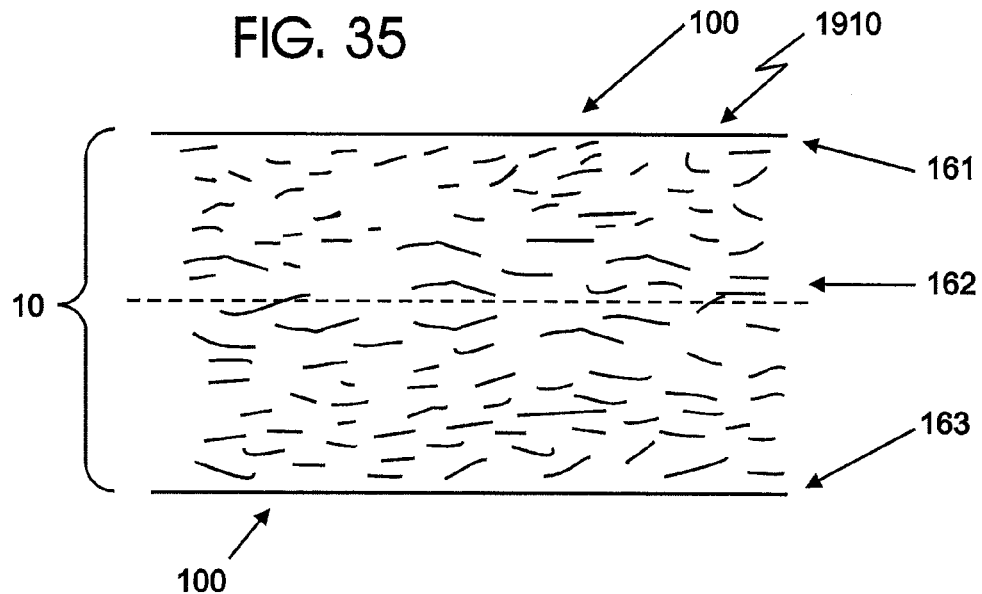
FIG. 35 is also a cross-section of an alternative embodiment in which the separately identified functional layers have been combined into a composite fibrous or foam structure having a gradient in pore size as one moves from the mid plane of the reservoir towards each face of the device.

FIG. 35 shows a cross-section of another device 1910 that incorporates a material with continuous gradients of pore structure. Rather than using different, discrete reservoir and covering materials, device 1910 uses a fibrous structure from which complete devices can be die cut. This fibrous structure may take the form of a thick mat of different fibers that are laid down in a web-forming machine capable of layering each fiber type at different horizontal planes in the total cross-section. Individual fiber layers are interblended at the interfaces between adjacent layers so that there is a smooth transition in fiber and porosity properties from one face of the mat through to the other. Fibers used in the cross-section of the composite are selected based upon their wetting and capillary behavior towards the flowable therapeutic formulation to be used. As shown in FIG. 35, the fibers at and near the approximate mid-plane 162 of the composite would define the reservoir region of the composite. As described in detail below, these fibers have properties that permit them to hold the flowable therapeutic formulation but not resist relatively larger capillary forces tending to drain the flowable therapeutic formulation away. Moving away from the mid-plane reservoir region 162, through cover regions 161, 163, and towards each face surface 100, the type and character of fibers changes progressively causing flowable therapeutic formulation to be drawn towards each surface 100 until each surface is saturated and the flow reaches equilibrium.

Figure 36:
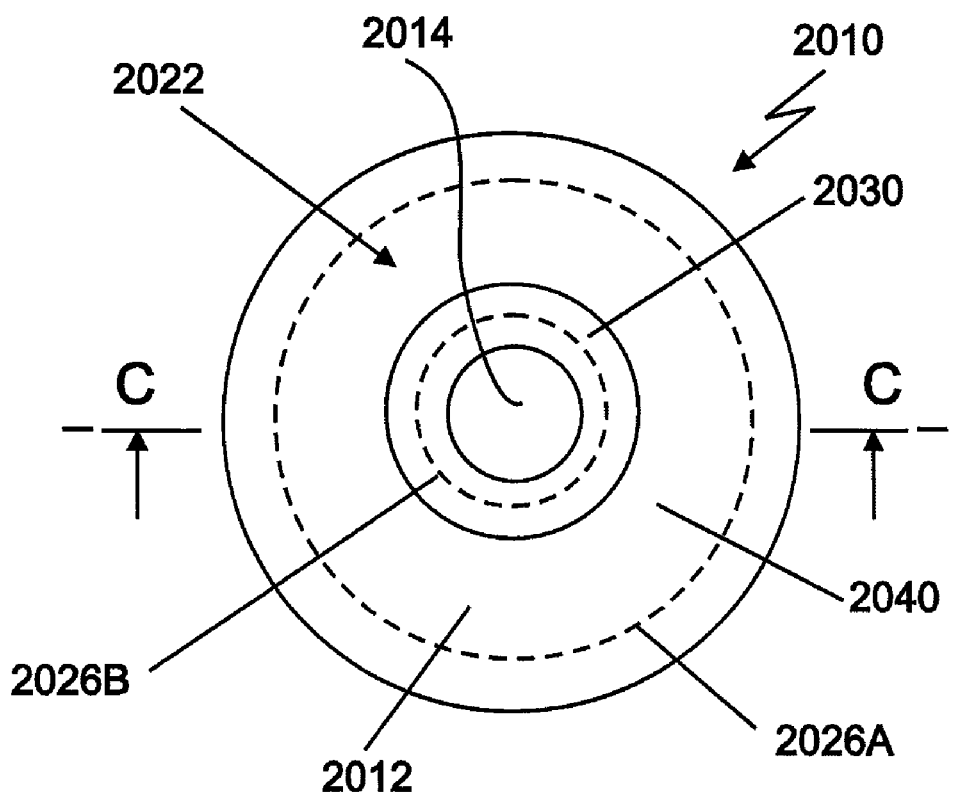
FIG. 36 is a plan view of a donut-shaped device. The donut hole can facilitate removal of the device and the shape can focus delivery of a flowable therapeutic formulation to the cervix.
Figure 37:
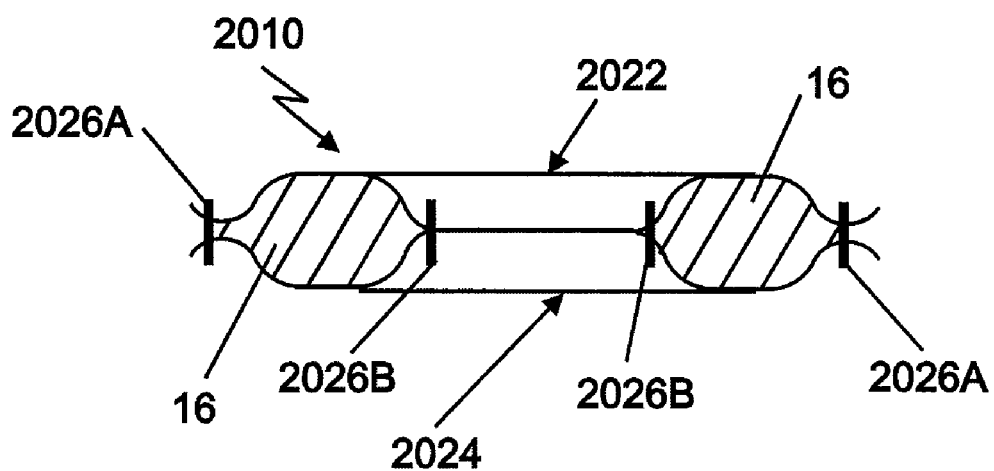
FIG. 37 is a sectional view of the device of FIG. 36, taken substantially at line C-C.

FIGS. 36 and 37 show another device 2010 that has a relatively flat, circular donut-shape that includes a ring-shaped body portion 2012 and a central opening 2014. Device 2010 includes top and bottom covers 2022 and 2024, respectively, that envelope a ring-shaped reservoir 16. The device may be formed with circular seals at 2026A and 2026B, similar to seal 26 of the device of FIGS. 1 and 2. Device 2010 is configured for two purposes: (1) so that the hole 2014 can be easily grasped for removal; and/or (2) for use to surround the cervix and to provide preferential surface wetting of the device in the region that is in contact with the cervix. For the second purpose, the inward, central region 2030 of device 2010 can be designed to produce significant wetting for delivery of flowable therapeutic formulation to the cervix, while the remaining outer region 2040 is designed to produce less wetting. This focused wetting of the covering of device 2010 may be achieved by a number of means. In one embodiment, a repellent agent (not shown) may be printed on the covering material 2022 and/or 2024 in the outer region 2040. In another embodiment, an internal baffle (not shown) may be provided in the internal structure of device 2010 to completely or partially separate the covering in outer region 2040 from the reservoir. These and other structures may be devised consistent with the teachings herein to achieve the focused delivery of flowable therapeutic formulation to the cervix. It will be understood that other geometries may be used to focus delivery to other areas of the vagina.

The reservoirs of the insertable devices 10 through 2010 described above in conjunction with FIGS. 1-37 serve as the primary storage area for the flowable therapeutic formulations that are dispersed by the devices. In this regard, the reservoir preferably is formed of a material designed to release the contained flowable therapeutic formulation from the reservoir, into and through the device covering. While not specifically shown in the figures, the covering is made from one or more layers of porous material that draw the therapeutic agent from the reservoir, maintaining the outer surfaces of the covering of the device preferentially wet. Thus, when the device is in vaginal use, typically at or near the cervix, the characteristics of the reservoir and covering materials serve to drive the therapeutic agent in a flowable therapeutic formulation to the surface of the device to thereby continuously deliver the agent to the vaginal surfaces.

Reservoir and Covering Materials and Properties of Therapeutic Formulations

In the various embodiments described herein, the flowable therapeutic formulation is caused to flow preferentially in one direction, and without the need for application of external pressures.

The inventors have found that the liquid of the therapeutic formulation will move into a porous wettable medium such as a fibrous pad by capillary suction. For flowable materials having a liquid phase, the capillary suction created by the pores of the pad acting on the fluid is described by the following Laplace equation:

$$P = \frac{2\gamma \cos\theta}{R_c}$$

Where $P$ = the capillary suction created;

$\gamma$ = the surface tension of the liquid phase of the flowable material;

$\theta$ (Theta) = the contact angle formed between the liquid phase of the flowable material and the porous media material; and $R_C$ = is the effective capillary radius of the internal pore structure of the structure.

When the capillary suction is positive, the therapeutic formulation is drawn into the porous structure. When it is negative, then the porous structure is exerting a force on the fluid trying to expel the fluid from the pores.

When two fibrous or otherwise porous structures 'A' and 'B' are in contact and include the same wetting liquid contained within their own respective pore structures, no movement of liquid will occur if the capillary suction forces exerted by each structure on the contained liquid are equal. However, if there are differences between contact angles, effective capillary radius for the two media in contact and containing the same fluid, then the Laplace equation predicts and measure liquid partitioning between the two media. When equilibrium occurs, $$P\,(\text{MEDIA}\,A) = P\,(\text{MEDIA}\,B).$$

That is, liquid does not flow from one structure to the other. Creating an imbalance between the two structures will cause liquid to flow until the capillary suction forces exhibited by each structure are again in balance. Thus, with the same fluid in 'A' and 'B', manipulating the effective capillary radius pore size distribution and contact angle for media 'A' to create a higher capillary suction than that in media 'B' will cause liquid to flow from 'B' to 'A'. Thus,

| MEDIA A | MEDIA B |
|---|---|
| CAPILLARY SUCTION FORCE | |
| $\dfrac{\cos\theta}{R_{CA}}$ > | $\dfrac{\cos\theta}{R_{CB}}$ |

Where $R_{CA}$ = Capillary radius in media 'A'.

$R_{CB}$ = Capillary radius in media 'B'.

Liquid will be drawn from media 'B' into media 'A' until the capillary suction of Media 'A' equals the opposing capillary suction forces of Media 'B', and usually because all attractive pores are filled.

The capillary suction force created by media acting on a liquid is proportional to $$\frac{\cos\theta}{R_c}$$

and can be increased by making the effective capillary radius very small. Capillary suction force can also be increased by selecting a media such that the value of $\cos\theta$ (the wetting angle) is as large as possible; i.e., a value of +1, or a wetting angle of zero between media surface and wetting liquid. Conversely, the suction force can be reduced and even made negative by selecting a porous media in which the wetting angle is between 90 degrees and 180 degrees ($\cos\theta$ between 0 and −1).

Smaller effective capillary radii also serve to make the negative capillary suction forces higher when the wetting angle is between 90 and 180 degrees.

In terms of the devices disclosed herein, and as will be appreciated, there are numerous combinations of capillary equation factors which may be manipulated to cause flow from the reservoir to the surface of the device, and to replenish liquid transferred from the surface of the device onto vaginal tissue. For example:

1. If the device reservoir and device covering have identical effective capillary radii, and the liquid contact angle is below about 60 degrees for the covering and greater than about 60 degrees for the reservoir, flowable material will be forced from the reservoir to the covering whenever pore space within the covering is available.
2. If a small pore size covering and large pore size reservoir are made from the same material and have the same wetting angle below about 90 degrees, and preferably below about 60 degrees with the flowable material, then capillary forces will move the flowable material from large pores in the reservoir to smaller pores in the covering.
3. If the reservoir and covering have identical effective capillary radii, and the liquid contact angle with the flowable material is above about 110 degrees for the device covering and greater than about 140 degrees for the reservoir, flowable material will be forced from the reservoir and into pores in the covering.
4. If a covering containing large pores surrounding a reservoir of small pores are made from the same material and have the same wetting angle above 90 degrees and preferably above 110 degrees with the flowable material, then capillary forces will move the flowable material from small pores in the reservoir to larger pores in the covering.

Therefore, it will be appreciated that the reservoir may be configured from a variety of materials including cellulosic and synthetic fibers and filaments, bleached rayon, cross-linked cellulose based fibers, porous foams, and super-absorbent gels, with the preferred choice being relatively coarse and stiff textile fibers. The selected materials may in some cases be formed into knitted, woven, and/or non-woven textile structures. In certain embodiments, the materials may be biodegradable. By relatively coarse, we mean fibers or filaments whose denier is typically in a range of about 2 to about 100 denier per filament. Because the device is subject to compressive forces in use and may be subject to compressive forces while in its package, it is desirable that the reservoir's structure be compressively resilient, sufficient to hold the internal surfaces of the reservoir enveloping covering apart and thus preventing excessive release of the flowable therapeutic formulation from the reservoir when the device is compressed and while in a watertight package prior to use. It is also desirable to package the device with little or no air in the package in order to help minimize flow of the formulation out of the device during storage.

Reservoirs configured from fibrous structures in the form of sliver, roving, knit, knitted, woven, nonwoven, spun-bond, meltblown, thermal bonded, needled, high loft, reticulated foams, films, or similar structures are contemplated. It is important that the reservoir have sufficient internal-connected spaces within its structure to contain flowable therapeutic formulation. Furthermore, it is desirable that the various structures of the reservoir have natural-surface finishes, as made or added intentionally, so that the reservoir can store and subsequently dispense the therapeutic agent by both capillary forces and physiologic pressures. More particularly, the various structures may be formed from synthetic fibers that are spun without the addition of spinning or lubricating finishes which are normally added to the hot, newly spun fibers as they exit the spinnerette. The natural surface characteristics of the newly spun fibers are generally water repellent which ultimately aids in repelling the applied therapeutic formulation, rather than holding it, during use of the device constructed from such fibers. For fibers that are naturally wettable, an intrinsically water repellent material may be sprayed onto the fibers to create a suitably repellent matrix surface that promotes migration of the therapeutic formulation toward the vaginal tissue. It has been found, for example, that a suitable reservoir may be constructed from a high loft batting, one half inch thick and made from coarse denier polyester fiber, bonded with a binder adhesive and sold as TX 13, manufactured by the Carpenter Company, Taylor, Tex.

It will be understood that in certain embodiments the chemical and physical characteristics of the material forming the reservoir may be engineered to be phobic relative to the flowable therapeutic formulation in order to facilitate the release of the flowable therapeutic formulation as it migrates to the surrounding covering. Materials that are easily wetted by the flowable therapeutic formulation are generally less suitable for reservoir construction because the flowable therapeutic formulation would be attractively held within the reservoir due to capillary forces. These forces would cause the therapeutic agent to remain within the reservoir and are increased when the total device is compressed, as is more likely to occur when the device is contained within the vagina. This phenomenon can be attributed to the capillary forces attracting the therapeutic material to the storage reservoir and increasing as the device is compressed. On compression, the pores within the storage reservoir are reduced in dimensions. Decreasing the capillary dimensions in an absorbent material where the absorbed, flowable therapeutic formulation wets the capillary surfaces causes the interfacial forces between wetting flowable therapeutic formulation and capillary surfaces to increase according to the Laplace equation, as will be appreciated by those skilled in the art. Therefore, it is generally desirable that the characteristics of the material comprising the reservoir be less retentive to the contained, flowable therapeutic formulation than the characteristics of the materials which comprise the covering surrounding the reservoir. Those skilled in the art will recognize that the result will be to facilitate the release of the flowable therapeutic formulation from the storage reservoir to the outer surface of the device covering.

Therefore, there are at least two physical mechanisms for inducing flowable therapeutic formulation to move from the reservoir to the covering by means other than compression:

1. Control of the contact angle between the flowable therapeutic formulation and the reservoir material, and control of the contact angle between the flowable therapeutic formulation and the covering material; and
2. Control of the interconnected pore sizes within the reservoir structure, and control of the interconnected pore sizes within the covering material.

In general, the reservoir material should have a nominal contact angle greater than that of the covering material. Both materials could have wettable-contact angles, but with the reservoir material having a higher contact angle with the flowable therapeutic formulation than that of the covering material. Alternatively, the reservoir material could have a nominally repellant finish and a flowable-material-contact angle greater than about 90 degrees. Thus the reservoir would have a degree of repellency towards the flowable therapeutic formulation while the covering material has a nominally wettable finish and a flowable-material-contact angle less than about 90 degrees.

Having a phobic reservoir may impose special considerations on the package in which the device is stored. Such a reservoir may tend to compress the flowable therapeutic formulation in the device unless countered by pressure from the package and/or atmosphere. If there is air in the package, this may be exacerbated by high altitude/low pressure situations such as air freight. Thus, it may be desirable in some situations to exclude air from the package. In addition, if the internal surface of the package is strongly hydrophobic, that will reduce the amount of flowable formulation that is released from the device during storage. To ensure that the maximum amount of the flowable formulation is reserved for flow after vaginal insertion of the device, the device may include wicking fibers in the reservoir to insure that pores are well drained.

Reservoir and cover materials, and more specifically fiber surfaces, can be made hydrophobic by saturation with an adhesive non woven binder such as B.F. Goodrich Hycar 2600 X120 LRM and for which the level of hydrophobicity may be controlled by the addition of surfactants to the applied binder such as Aerosol OT. Cellulose fibers such as cotton, rayon and pulp may be made to be hydrophobic to a predetermined degree by treatment with debonding agents such as quaternary ammonium compounds used in papermaking, by the use of fabric softener finishes, or by the addition of finishes designated as repellant and hydrophobic. Such materials have very high contact angles when wet with both aqueous and oily materials and can be used to assist flow from the reservoir for therapeutic materials containing both aqueous and oleophobic components. A fiber finish sold by Omnova Performance Chemicals of Chester, S.C. USA as Sequapel AFC creates a surface finish which is both hydrophobic and oleophobic. In addition to driving flowable therapeutic formulation from the reservoir, such a finish may also prevent adsorption of expensive therapeutic materials by the reservoir material. Milder levels of phobicity can be provided on reservoir materials by using Omnova Performance Chemicals Sequasoft 69, which provides a contact angle with water of about 60 degrees.

While not limiting the materials from which the components of this device can be manufactured, it will be appreciated by those skilled in the art that fibers are a convenient starting and illustrative material from which to construct devices of this invention. This is also exemplary of how other materials, such as porous foams, apertured films, and other macroporous and microporous materials might be beneficially incorporated.

For any given fiber material, there is a measurable and defined contact angle when it is wet by a flowable therapeutic formulation. Bleached cellulose fibers have a very low, essentially zero contact angle. On the other hand, polypropylene, polyethylene, and polytetrafluorethylene fibers have very high contact angles, between about 90 and about 180 degrees. Also, they are essentially repellent when the nature of the flowable therapeutic formulation is water-based. Polyester fibers are borderline wettable with water-based flowable therapeutic formulations with a contact angle around 90 degrees. Applying a finish to any one of these fibers can alter the contact angle of flowable therapeutic formulation in contact with them. Applying waxy or olefinic materials to the surface of intrinsically wettable fibers, such as bleached cotton, can render the surface less hydrophilic, which can be demonstrated by evidence of a higher contact angle. Conversely, an intrinsically non-wettable fiber can be made less repellent by the application of finish. It can also be made to be very wettable by the flowable therapeutic formulation (i.e., a lowering of the wetting contact angle to approach zero). For example, one phobic material that may be used with a therapeutic agent such as an aqueous anti-HIV formulation would be a quaternary ammonium fabric softener which imparts a mildly repellent character to a cellulose surface.

Covering layers such as 22, 24, may be formed of a suitable material such as woven material, nonwoven material made from staple or from continuous filaments, fiber mats, knit materials, apertured films, porous papers, or like materials. Apertured films may be produced by laser, heat or vacuum aperturing devices and are commercially available as diaper and feminine hygiene top sheets, sold by Pantex International and by Tredegar Film Products. For coverings manufactured by textile, paper, or nonwoven processes, rayon, cotton, polyesters biodegradable fibers, and traditional tampon fibers such as bleached cotton, bleached rayon, trilobal rayon, acetate, high and wet, modulous rayons, lycocell rayons, etc., generally having deniers at or below about 2.0 denier per filament are suitable. As discussed above, it is desirable that the covering material have a suitable pore structure, porosity, and surface character to facilitate driving the flowable therapeutic formulation containing therapeutic agent to the outside surface via capillary action.

In many applications of the invention, as discussed above, the primary mechanism that delivers the flowable therapeutic formulation from the reservoir to the outer surface of the device is the presence of capillary forces between the component layers comprising the device. Flow from the reservoir to the outer surface of the device is determined by the demand created at the device surface (i.e., by making the pore structure of the device's outer surface exhibit a greater capillary force on the flowable therapeutic formulation contained within the reservoir than the forces exerted upon the flowable therapeutic formulation by the materials comprising the reservoir and attempting to retain it within the reservoir).

In the embodiments of FIGS. 1 through 7 in particular, the desired directional flow of flowable therapeutic material is achieved by selecting materials for the reservoir 16 such that the reservoir will be less wettable than the outer cover or covers. Thus, the material for covers 22, 24 is generally chosen to be compatible with the reservoir material and to be more wettable than the reservoir when in contact with the same flowable therapeutic formulation containing therapeutic material. More specifically, in embodiments such as those shown in FIGS. 1-7, the interconnected network of pores within the reservoir and the surrounding contact cover or covers creates a gradient of capillary forces that drives the delivery of the flowable therapeutic formulation to the outer surface of the external covering of the device. Typically, this works by the combination of relative-pore dimensions and capillarity characteristics of the materials that comprise the reservoir and cover or covers. For example:

A device such as illustrated in FIGS. 1 and 2 is selected for delivery of a water-based, thickened solution of a therapeutic agent having a viscosity of about 300 centipoises.

The reservoir of the device takes the form of an open, structured material with interconnected internal spaces ("pores"). The mean pore size diameter as determined by a porosimeter is in the range from about 100 microns to about 2000 microns, with a mean pore size in the range from about 200 to about 1500 microns being preferred. The reservoir material has a material-surface-contact angle with the flowable therapeutic formulation between about 20 degrees and about 60 degrees. The thickness of the reservoir is in the range from about one quarter inch to about one inch, with an average thickness of about ⅜ inch being preferred for this Example.

A compatible covering for enveloping the above reservoir is formed of a hydroentangled and fibrillated Lyocell rayon non-woven material having a basis weight in the range from about 20 to about 60 grams per square meter, a thickness between about 10 and about 40 thousandths of an inch, and, a contact angle with the flowable therapeutic formulation in the range of about 0 to about 25 degrees. The mean pore size diameter of the covering material is in the range from about 20 microns to about 150 microns, with a preferred pore size diameter between about 40 microns to about 80 microns for this Example.

A suitable covering material matching the above characteristics is manufactured by DuPont as a 24 mesh spun-lace fabric, Style 8654, weighing 1.45 ounces per square yard (49 grams per square meter) and composed of 100% Lyocell fiber. Alternatively, one could use a similar DuPont non-woven fabric, Style 8423 weighing 2.30 ounces per square yard (78 grams per square meter) and composed of 70% rayon and 30% polyester fiber.

The overall diameter of the device may be about one to about three inches.

A structure as described immediately above can contain from about 3 ml to about 25 ml of flowable therapeutic formulation.

In view of the foregoing, it will be appreciated that the design parameters for the reservoir and covering materials of the embodiments of the present invention may include:
1. The viscosity of the flowable therapeutic formulation;
2. The delivery rate desired;
3. The volume of flowable therapeutic formulation to be delivered;
4. The intrinsic wettability of the reservoir material by the flowable therapeutic formulation;
5. The intrinsic wettability of the covering material by the flowable therapeutic formulation;
6. The difference in wettability between the reservoir and covering materials;
7. The level of accumulated wetness required to be present on the external surface of the covering; and
8. The pore size distribution in the reservoir and in the covering layer(s).

As will be appreciated, the specific exemplary dimensions and values of the various parameters are not limiting to the various embodiments described herein.

The selection of reservoir and cover materials may be dictated by the availability of material, material costs, manufacturing costs, the unique properties of the flowable therapeutic formulation and by manufacturing restrictions. In this regard, bleached cotton knit or woven fabrics may be a suitable choice for the cover. Alternatively, a high speed manufacturing operation may require the availability of covering and reservoir materials which can be heat sealed and/or die cut. Suitable heat sealable covering materials include those which are biodegradable, have low contact angles with water, and which wet and store water-based fluids, and are available for example as tea bag material, manufactured in various weights and porosities by, for example, Ahlstrom Corporation, Fiber Composites Division, Windsor Locks, Conn. Such products are generally available for use with different and adjustable types of heat sealing resins.

Reservoirs, as previously described, may be created from structures that are thermoplastic such that the application of heat and pressure will create a perimeter seal. Thermoplastic materials in fiber or other porous form such as polyester, polypropylene, polyurethane and polyethylene resins and blends thereof may be used to create reservoirs with this kind of perimeter seal, as can many reticulated foams or interconnected fibers. Additionally, polyvinyl acetal foams, already used in medical absorbency products, may be modified in mean cell pore size and surface wetting characteristics to create a suitable reservoir.

Where it is necessary to deliver higher total volumes of the therapeutic agent, the reservoir and covering materials may generally be formed so that the reservoir has a flowable therapeutic formulation holding capacity of between about 3 grams and about 30 grams of fluid per gram of material, and the covering has a flowable therapeutic formulation holding capacity of between about 2 grams and about 5 grams of fluid per gram of material. In a fibrous reservoir, the void volume can be maintained by the use of a proportion of bicomponent heat bonding fibers which, when heated in situ, create stable and somewhat compression resistant pores.

The nature of the therapeutic formulation may take the form of a simple gel similar to KY jelly, a flowable phase agent, a semi-solid material, a breakable emulsion, a rheopectic gel, or other suitable flowable form which can be contained within the structure of the reservoir and driven to the outside surface of the covering as described herein.

As discussed above, the external surface characteristics of the insertable device are designed for ease of insertion and comfort of the user, particularly with respect to prewetting of the surface of the device prior to insertion. In this regard, it has been found that the covering of the device can be symmetrical about the reservoir or it may be asymmetrical. For an asymmetrical covering, the outer material on the cervical side may be chosen to be easily wet and/or non-abrasive and easy to insert with a finger, i.e., no need for traditional piston-type applicators that are used with most tampons. Where desired, a lubricating agent may be utilized to facilitate insertion. Lubricating agents for mucosal surfaces are well known to those skilled in the art, and include but are not limited to glycerin, propylene glycol, dimethicone copolyol, and various mixtures thereof.

While the therapeutic agent is generally applied directly to the reservoir of the device, some pretreatment of layers can be used to aid in later dispersion of the agent. These pretreatment agents, while not limited to the following, may include prewetting the reservoir fibers using de-ionized water so that more of the therapeutic agent can be physically free and only held in by the pore structure of the reservoir. Further, the reservoir may have outer layers that are biofilms designed so that the environment of the vagina decomposes these films, and the active agent is dispersed immediately or on a timed or sustained release schedule.

As part of a low cost manufacturing process, the therapeutic formulation may be applied into or onto the device after the device has been individually packaged, but before the package is sealed. Most flowable therapeutic formulations will then diffuse throughout the device over a period of hours or days after the package is sealed.

Test Data

A standard flowable therapeutic formulation of the type which may be used was used to measure the migration of an agent, such as sodium chloride, in a gel placed within the device reservoir, through the covering, and into deionized water. A series of circular devices were constructed by sewing a woven bleached cotton fabric covering around a high loft polyester fiberfill reservoir. The reservoir material for this prototype device was 100% new polyester material, high-loft batting, ½ inch thick, TX 13, made by Carpenter Company, Tyler, Tex. A formulation of 0.9% sodium chloride in KY Jelly (Personal Products Company, Skillman, N.J.), which contains purified water, glycerin, hydroxyethylcellulose, chlorhexidine gluconate, gluconolactone and methylparaben, was prepared. In addition to the simple addition of sodium chloride to KY Jelly, two less viscous formulations were prepared by diluting the KY Jelly 1 to 1 and 1 to 3 with purified water. These flowable formulations were injected into the device reservoir.

Preliminary work on agent migration characteristics was done by positioning each device about 10 centimeters below the surface of an agitated deionized water bath at 37° C. This water bath testing was done using standard pharmaceutical dissolution methods, as described in USP 28, section 711, "Dissolution."

Figure 38:
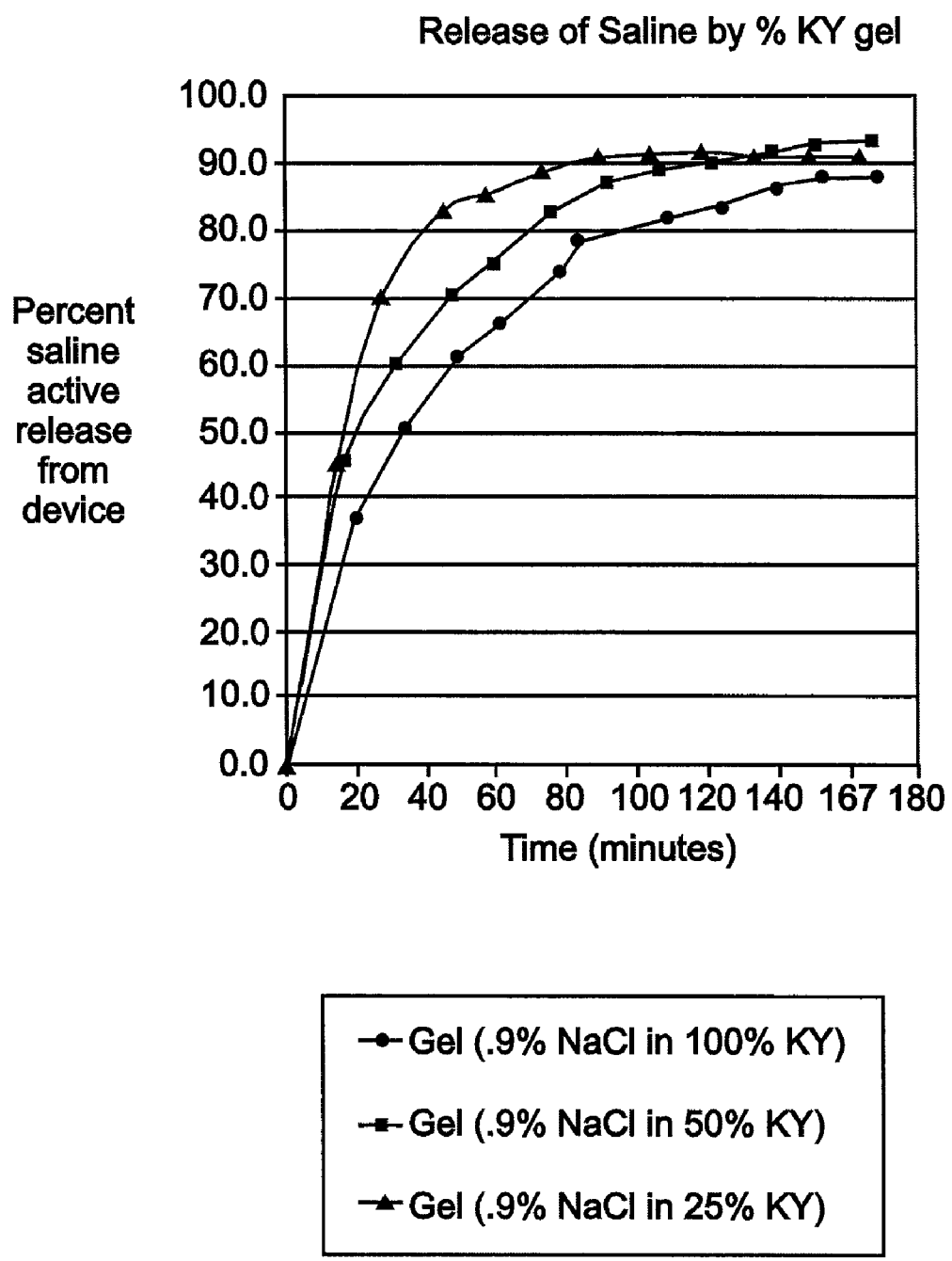
FIG. 38 is a graph showing the speed of release of sodium chloride from a test device, by differing concentrations of a gelling agent in the formulation, using a USP standard water bath dissolution apparatus.

Migration of saline from the device was measured by monitoring the increase in conductivity of the bath. Data (FIG. 38) show that the release of sodium chloride from the device is inversely related to the viscosity of the formulation. With the marketed K-Y jelly formulation, about 37% of the sodium chloride was released in about 20 minutes. With lower viscosity formulations, initial release was more rapid, and about 50% to 60% of the sodium chloride was released in about 20 minutes.

Figure 39:
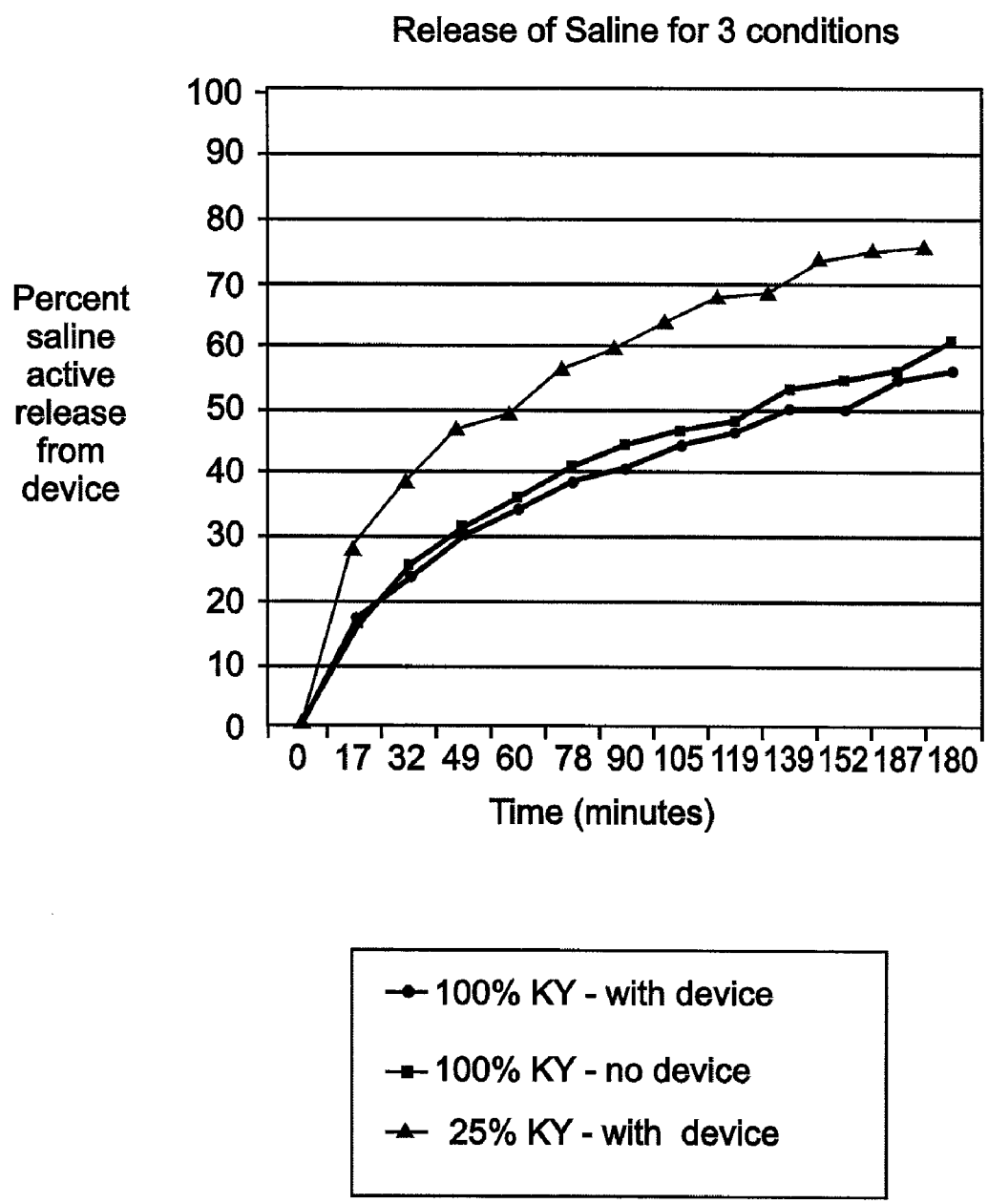
FIG. 39 is a graph comparing the release of sodium chloride from a simple gel compared with its release from a similar but less concentrated gel in a test device, using a USP standard water bath dissolution apparatus.

In a second experiment, using a basket dissolution apparatus (USP 28, section 711, "Dissolution") in order to contain a simple gel formulation, the diffusion of sodium chloride from KY Jelly, was compared with its diffusion from 100% KY Jelly and a 25% KY Jelly formulation, both contained within the same device described above in connection with FIG. 38. Data in FIG. 39 suggest that sodium chloride diffusion from the 100% KY Jelly within the device was similar to release from the KY Jelly without a device. Diffusion from the 25% KY Jelly within the device was more rapid than from the plain KY Jelly. Specifically, at about 100 minutes, the estimated release was about 46% from the plain KY Jelly, about 43% from KY Jelly within the device, and about 62% from 25% KY Jelly formulation within the device.

The methods described above and the data in FIGS. 38 and 39, illustrate methods which could be used to evaluate the release of various flowable therapeutic agents from the device.

Typical flowable therapeutic formulation examples suitable for this device are as follows:

Anti HIV Flowable Therapeutic Formulation Compositions

Numerous microbicides have been developed or are under investigation for potential human use for HIV prevention and are described in numerous scientific publications. For example, tenofovir has been developed as a 1% vaginal gel for prevention of sexual transmission of HIV.

Representative Antifungal Formulation: The addition of therapeutic agents such as of 1% Tioconazole, 1% Butaconazole, or 1% Flucanazole to a flowable-material formulation provides a device capable of dispersing antifungal material to vaginal tissue.

Representative Spermicidal Formulation: As an example, the addition of 0.95% nonoxynol-9 to a formulation yields a flowable therapeutic formulation which will dispense from the device and provide spermicidal properties to the vaginal fluids. Since N-9 has been shown to increase the risk of HIV infection, there is an active search for topical contraceptive agents for vaginal use, recently reviewed by Hughes et al (Hughes, L. M.; Griffith, R., and Aitken, R. J. The search for a topical dual action spermicide/microbicide. Curr Med Chem. 2007; 14(7):775-86.)

Device Insertion: As described above, digital insertion of the device may be facilitated through the use of one or more finger pockets or cut openings, such as pocket 39 illustrated in FIG. 16 and 17, or the slits illustrated in FIG. 21. The pocket may have several variations, including being integral with the outer material of the covering layer. The pocket may also be incorporated within the package itself. Further, the pocket may be constructed by the user through use of an adhesive tab/backing imparted to the carrier or package. Such a pocket, while designated a finger pocket, may be used with a number of inserter devices instead of a finger. Such devices may range from molded plastic, stick-type devices or hooks, to paper, rubber or ceramic inserters that would be designed to allow the user to place the device in the vagina without causing injury to the vaginal wall. The shape of the inserter, preferably, is such that the user will be able to position it for optimal placement of the device and therapeutic agent. The terms "digit" and "digital," as used herein, refer to a woman's fingers or to other means for inserting the carrier within the vagina through the use of an insertion device; for example, the plastic stick referred to above would act as a digit.

Also as noted previously, the device may be inserted using an inserter device similar or identical to commonly used piston-type cylindrical inserters that are used for tampons. However, while tampons are generally compressed within a cylindrical inserter device, and tampons expand substantially upon wetting, this invention is pre-wetted and would preferably be packaged in a fully wetted state, with minimal or no compression within the inserter device.

Male Version: Devices of this invention could also be designed to be inserted by being placed on the tip of a man's penis. Preferred embodiments for this method of insertion would be similar to the devices described above that have finger pockets, as shown in FIGS. 16 and 17. However, the size of the finger pocket would be larger in order to fit over the tip of the penis. A male version would also include a removal method, preferably a cord as illustrated in FIGS. 12 and 17. The size of a device for male use, however, would be larger.

The recent scientific literature suggests that the width of the tip of the erect penis is about 3.5 cm with a range of between about 2.6 to 4.5 cm, and a circumference of about 9.5 cm +/−1.5 cm. A device to fit on the tip of the penis of most men would thus require a finger pocket with an opening between about 5.0 cm and about 6.5 cm wide, dimension 1265 in FIG. 17a. In an embodiment for male use, the ratio of the length of the device to the width of the device could be decreased. The inner surfaces of the device can be made more slippery and less adherent to penile tissue than to vaginal tissue than the outer surfaces through the use of a non-woven composite material such as 30SR-Delnet/3.7NPET-E material, described above. Other slippery non-adherent surfaces typically associated with wound release characteristics and variously described as reticulated films, apertured films, surface treated films, and the like may also be employed to provide both a low friction and preferably low adherent surface and one that is also porous to the degree required. Control of porosity in the surface or composition of the male device permits one to increase the surface area of fluids as they are forced through the device structure, and thereby increase the opportunity for intimate mixing of ejaculate with therapeutic gel.

Chen, J.; Gefen, A.; Greenstein, A.; Matzkin, H., and Elad D. Predicting penile size during erection. Int J Impot Res. 2000 December; 12(6):328-33; and Schneider, T.; Sperling, H.; Lummen, G.; Syllwasschy, J., and Rubben, H. Does penile size in younger men cause problems in condom use? a perspective measurement of penile dimensions in 111 young and 32 older men. Urology. 2001 February; 57(2):314-8.

During insertion of the male device, some of the flowable formulation would be left on the vulva because of the pressure of insertion through the introitus on the sides of the penis and the device. The amount released at the introitis would depend partly on the viscosity of the formulation. Leaving some of the flowable formulation is desirable in order to prevent infection of the vulvar and introital surfaces. Too avoid leaving too much of the flowable formulation at the introitus or on the vulva, the device can be made with an extra fold or ridge in the material which could be made parallel to dimension 1250w, and near the middle of the device. Such a fold or ridge would act to collect flowable formulation squeezed out of the leading portion of the device during insertion, and would provide some protection against lateral pressures for the formulation in the immediately following part of the device.

Device Removal: Devices of this invention preferably include a removal cord or tape, longer than the cord associated with a typical tampon. The longer cord is used to prevent displacement or loss of the cord in the vagina during sexual intercourse. In certain embodiments, the cord may be placed between the outer layers of the device and bonded to the reservoir in a sealing process that is known to those skilled in the art. As discussed above, devices of the invention may also be formed without a removal cord.

For the development of the device with a particular therapeutic agent, several features of the design, such as fiber type or fiber derivatization, may be optimized to assure efficient vaginal delivery and to ensure that the therapeutic agent is compatible with the device, such that no adsorption onto the device occurs. The key mechanisms utilized to deliver a therapeutic agent such as a microbicide from the device into the vagina are 1) movement of the gel driven by the relatively hydrophobic core and the attraction of the relatively hydrophilic outer layer and 2) diffusion of the active ingredient.

For low molecular weight, water-soluble agents, both mechanisms, i.e. gel movement and diffusion, will serve to deliver the agent. Since low-cost bleached cellulosic fibers are commonly hydrophilic, a hydrophobic inner core composed of cellulosic fiber can be formed by chemically modifying the fiber surfaces, or by using unscoured washed cotton.

As the molecular size of the active ingredient increases, gel movement out of the device will be more important with regard to delivery. If the therapeutic agent is hydrophobic, which could potentially cause the agent to adsorb onto the fiber surfaces of a relatively hydrophobic core, the degree of hydrophobicity or oleophobicity of the core and outer layer can be readily adjusted by the use of various fiber coating processes known to those skilled in the art. Thus the level of core hydrophobicity may be altered to promote delivery. The level of hydrophobicity or oleophobicity of the materials used in the device may be characterized with contact angle measurements (1), water repellency tests (2), or by various infrared spectroscopy techniques (3).

(1) Castellan, G. W., "Physical Chemistry," Benjamin/Cummings, Menlo Park, 1983.
(2) AATCC, Technical Manual of the American Association of Textile Chemists and Colorists, Vol 70, 1995.
(3) Skoog, D. A., Leary, James J. "Principles of Instrumental Analysis," Saunders College, Fort Worth, 1992.

While the present invention has been described in connection with certain illustrated embodiments, it will be appreciated that modifications may be made without departing from the true spirit and scope of the invention.

We claim:

1. A device for insertion into the vagina to deliver a flowable therapeutic formulation to the vaginal surfaces, said device comprising:
   a) a reservoir comprising:
      i. a forward end for placement proximate a user's cervix, a trailing end facing opposite the cervix, and a peripheral edge;
      ii. a non-woven fibrous material throughout;
   b) a flowable therapeutic formulation contained within and completely saturating the reservoir throughout, wherein the non-woven fibrous material is hydrophobic relative to the flowable therapeutic formulation;
   c) a layer affixed proximate the peripheral edge of and substantially parallel to the reservoir, a finger pocket formed between said layer and said reservoir proximate the trailing end; and
   d) said reservoir and said flowable therapeutic formulation creating capillary forces causing the flowable therapeutic formulation to migrate to the outer surface of the reservoir.

2. The device of claim 1 wherein the flowable therapeutic formulation contains a therapeutic agent that is selected from the group consisting of hormonal and non-hormonal contraceptive agents, vaginal spermicides, vaginal microbicides, antibacterial agents, antifungal agents, antiviral agents, anti-HIV agents and anticancer agents, or combinations thereof.

3. The device of claim 1 wherein the flowable therapeutic formulation contains an agent selected from the group consisting of a soluble or dispersible flowable material, a flowable phase agent, and a semi-solid agent, or combinations thereof.

4. The device of claim 1 wherein the flowable therapeutic formulation comprises a soluble or dispersible flowable material in dry form which is activatable by the user by adding a liquid such as water, vinegar or mineral oil before insertion into the vagina.

5. The device of claim 1 in which the reservoir material comprises an assembly of fibers having interfiber spaces defining pores within which the flowable therapeutic formulation is contained.

6. The device of claim 5 wherein the reservoir comprises relatively coarse and stiff textile fibers.

7. The device of claim 5 wherein the reservoir comprises textile fibers whose denier is in the range from about 2 to about 100 denier per filament.

8. The device of claim 1 wherein the reservoir comprises a fibrous structure selected from the group consisting of sliver, roving, knit, knitted, woven, non-woven, spun-bond, melt-blown, thermal bonded, needled, high loft, reticulated foams and films.

9. The device of claim 1 in which the reservoir comprises an open celled or reticulated foam.

10. The device of claim 1 wherein the reservoir has a mean pore size diameter in the range from about 100 microns to about 2000 microns.

11. The device of claim 1 further comprising a covering of porous material enveloping at least a portion of the surface area of the reservoir.

12. The device of claim 1 wherein the finger pocket is dimensioned to receive at least the tip portion of a human penis.

13. The device of claim 1 wherein the pocket is panduriform-shaped.

14. The device of claim 1 wherein the layer affixed proximate the peripheral edge of the reservoir comprises a smooth inner surface.

15. The device of claim 1 wherein the forward end of the reservoir is arcuate-shaped.

16. The device of claim 1 further including a withdrawal cord affixed proximate the trailing end of the reservoir.

* * * * *